US011519899B2

(12) United States Patent
Fraser et al.

(10) Patent No.: US 11,519,899 B2
(45) Date of Patent: Dec. 6, 2022

(54) METABOLOMICS PROFILING OF CENTRAL NERVOUS SYSTEM INJURY

(71) Applicant: LONDON HEALTH SCIENCES CENTRE RESEARCH INC., London (CA)

(72) Inventors: Douglas Dale Fraser, London (CA); Robert Bartha, London (CA); Arthur Brown, London (CA); Tanya Charyk Stewart, London (CA); Mark Daley, London (CA); Gregory A. Dekaban, London (CA); Timothy Doherty, London (CA); Lisa Fischer, London (CA); Jeffrey Holmes, London (CA); Ravi Menon, London (CA); J. Kevin Shoemaker, London (CA); Charles A. Rupar, London (CA)

(73) Assignee: LONDON HEALTH SCIENCES CENTRE RESEARCH INC., London (CA)

( * ) Notice: Subject to any disclaimer, the term of this patent is extended or adjusted under 35 U.S.C. 154(b) by 1285 days.

(21) Appl. No.: 15/560,056

(22) PCT Filed: Mar. 18, 2016

(86) PCT No.: PCT/CA2016/050310
§ 371 (c)(1),
(2) Date: Sep. 20, 2017

(87) PCT Pub. No.: WO2016/149808
PCT Pub. Date: Sep. 29, 2016

(65) Prior Publication Data
US 2018/0074038 A1 Mar. 15, 2018

Related U.S. Application Data

(60) Provisional application No. 62/135,886, filed on Mar. 20, 2015.

(51) Int. Cl.
| | |
|---|---|
| *G01N 33/487* | (2006.01) |
| *G16B 40/00* | (2019.01) |
| *G01N 33/483* | (2006.01) |
| *G01N 33/68* | (2006.01) |
| *G16C 20/70* | (2019.01) |
| *G01N 24/08* | (2006.01) |
| *G16B 40/20* | (2019.01) |
| *G16B 40/30* | (2019.01) |
| *G16B 40/10* | (2019.01) |

(52) U.S. Cl.
CPC ......... *G01N 33/487* (2013.01); *G01N 33/483* (2013.01); *G01N 33/6896* (2013.01); *G16B 40/00* (2019.02); *G16C 20/70* (2019.02); *G01N 24/08* (2013.01); *G01N 2570/00* (2013.01); *G01N 2800/28* (2013.01); *G01N 2800/2871* (2013.01); *G16B 40/10* (2019.02); *G16B 40/20* (2019.02); *G16B 40/30* (2019.02)

(58) Field of Classification Search
CPC ............... G01N 33/487; G01N 33/483; G01N 33/6896; G16B 40/00; G16C 20/70
USPC ......................................................... 702/19
See application file for complete search history.

(56) References Cited

U.S. PATENT DOCUMENTS

2016/0209428 A1* 7/2016 Naviaux ............ G01N 33/6848

FOREIGN PATENT DOCUMENTS

| EP | 2492690 | 8/2012 |
|---|---|---|
| WO | 2013060788 | 5/2013 |
| WO | 2015/027116 | 2/2015 |

OTHER PUBLICATIONS

Braverman NE, Moser AB. Functions of plasmalogen lipids in health and disease. Biochim Biophys Acta 2012; 1822(9): 1442-52.
Bujak R, Struck-Lewicka W, Markuszewski MJ, Kaliszan R. Metabolomics for laboratory diagnostics. Journal of pharmaceutical and biomedical analysis 2014.
Farooqui AA, Horrocks LA, Farooqui T. Glycerophospholipids in brain: their metabolism, incorporation into membranes, functions, and involvement in neurological disorders. Chemistry and physics of lipids 2000; 106(1): 1-29.
Glaviano NR, Benson S, Goodkin HP, Broshek DK, Saliba S. Baseline SCAT2 Assessment of Healthy Youth Student-Athletes: Preliminary Evidence for the Use of the Child-SCAT3 in Children—Younger Than 13 Years. Clin J Sport Med 2015; 25(4): 373-9.
Guskiewicz KM, Register-Mihalik J, McCrory P, McCrea M, Johnston K, Makdissi M, et al. Evidence-based approach to revising the SCAT2: introducing the SCAT3. Br J Sports Med 2013; 47(5): 289-93.
Harmon KG, Drezner JA, Gammons M, Guskiewicz KM, Halstead M, Herring SA, Kutcher JS, Pana A, Putakian M, Roberts WO. American Medical Society of Sports Medicine position statement: Concussion in sport. British Journal of Sports Medicine. 2013;47(1):15-26.

(Continued)

*Primary Examiner* — Jerry Lin
(74) *Attorney, Agent, or Firm* — Eduardo Krupnik

(57) ABSTRACT

A method of diagnosing central nervous system injuries such as acquired brain injury (ABI) and/or acquired spinal cord injury (ASI), including mild TBI (concussion or blast wave), mild ASI (contusion, stretch or partial cord transection), non-TBI brain injury and/or non-TSI spinal cord injury in a subject (animal or human). The method includes (a) obtaining a biological test sample from the subject, identifying metabolites in the subject's sample using metabolomics thereby obtaining a subject's metabolite matrix and generating a subject's profile using the patient's metabolite matrix; and (b) using multivariate statistical analysis and machine learning to compare the subject's profile with predetermined set of profiles of CNS injuries and a predetermined set of profiles of controls to determine if the subject has a CNS injury.

21 Claims, 8 Drawing Sheets

(56) References Cited

OTHER PUBLICATIONS

Halstead ME, Walter KD, Council on Sports M, Fitness. American Academy of Pediatrics. Clinical report—sport-related concussion in children and adolescents. Pediatrics 2010; 126(3): 597-615.
Blast Injuries: Traumatic Brain Injuries from Explosions, BrainLine, Oct. 19, 2010, https://www.brainline.org/article/blast-injuries-traumatic-brain-injuries-explosions.
Jeter CB, Hergenroeder GW, Hylin MJ, Redell JB, Moore AN, Dash PK. Biomarkers for the diagnosis and prognosis of mild traumatic brain injury/concussion. Journal of neurotrauma 2013; 30(8): 657-70.
Karlin AM. Concussion in the pediatric and adolescent population: "different population, different concerns". PM R 2011; 3(10 Suppl 2): S369-79.
Lovell MR, Collins MW, Iverson GL, Johnston KM, Bradley JP. Grade 1 or "ding" concussions in high school athletes. Am J Sports Med 2004; 32(1): 47-54.
Lovell MR, Solomon GS. Neurocognitive test performance and symptom reporting in cheerleaders with concussions. J Pediatr 2013; 163(4): 1192-5 e1.
McCrory P, Meeuwisse W, Aubry M, Cantu B, Dvorak J, Echemendia RJ, et al. Consensus statement on concussion in sport—the 4th International Conference on Concussion in Sport held in Zurich, Nov. 2012. Clin J Sport Med 2013; 23(2): 89-117.
Meier TB, Brummel BJ, Singh R, Nerio CJ, Polanski DW, Bellgowan PS. The underreporting of self-reported symptoms following sports-related concussion. J Sci Med Sport 2015; 18(5): 507-11.
Morrison G, Fraser DD, Cepinskas G. Mechanisms and consequences of acquired brain injury during development. Pathophysiology 2013; 20(1): 49-57.
Papa L, Ramia MM, Edwards D, Johnson BD, Slobounov SM. Systematic review of clinical studies examining biomarkers of brain injury in athletes after sports-related concussion. Journal of neurotrauma 2015; 32(10): 661-73.
Pellman EJ, Lovell MR, Viano DC, Casson IR. Concussion in professional football: recovery of NFL and high school athletes assessed by computerized neuropsychological testing—Part 12. Neurosurgery 2006; 58(2): 263-74; discussion—74.
Rosenfeld, et al., Lancet Neurol. Sep. 2013;12(9):882-93.
Shouval R, Bondi O, Mishan H, Shimoni A, Unger R, Nagler A. Application of machine learning algorithms for clinical predictive modeling: a data-mining approach in SCT. Bone marrow transplantation 2014; 49(3): 332-7.
Sikoglu EM, Liso Navarro AA, Czerniak SM, McCafferty J, Eisenstock J, Stevenson JH, et al. Effects of Recent Concussion on Brain Bioenergetics: A Phosphorus-31 Magnetic Resonance Spectroscopy Study. Cogn Behav Neurol 2015; 28(4): 181-7.
Stewart TC, Gilliland J, Fraser DD. An epidemiologic profile of pediatric concussions: identifying urban and rural differences. The journal of trauma and acute care surgery 2014; 76(3): 736-42.
Toledo E, Lebel A, Becerra L, Minster A, Linnman C, Maleki N, et al. The young brain and concussion: imaging as a biomarker for diagnosis and prognosis. Neurosci Biobehav Rev 2012; 36(6): 1510-31.
Van Der Maaten L, Hinton G. Visualizing data using t-SNE. J Mach Learn Res 2008; 9(11): 2579-605.
Dumas, M-E, Davidovic, L, Metabolic profiling of central nervous system diseases: metabolites bring insights into brain dysfunctions, J. Neuroimmuc. Pharmacol, 2015 (10), 402-424.
Viant, MR, Lyeth, BG, Miller, MG, Berman, RF, An NMR metabolomic investigation of early metabolic disturbances following traumatic brain injury in a mammalian model.
International Search Report and Written Opinion of the International Searching Authority of PCT/CA2016/050310.

\* cited by examiner

METABOLOMICS PROFILING OF CENTRAL NERVOUS SYSTEM INJURY

CROSS REFERENCE TO RELATED APPLICATIONS

This application is a national stage application under 35 U.S.C. 371 of International Application No. PCT/CA2016/050310, filed Mar. 18, 2016, which in turn claims the benefit under 35 U.S.C. 119(e) of U.S. Provisional Ser. No. 62/135,886, filed Mar. 20, 2015, the contents of each of which are hereby incorporated by reference into the present disclosure.

FIELD OF THE INVENTION

The field of this invention relates to metabolomics and methods of diagnosing injuries of the central nervous system (CNS) including all brain spinal cord injuries. More specifically, the present invention relates to metabolomics and methods of diagnosing: mild traumatic brain injury, including concussion and blast injury; mild spinal cord injury, including injuries caused by spine hyperflexion, hyperextension, rotation, lateral stress, compression, distraction and spinal cord partial transection; and non-traumatic CNS injuries caused by strokes, poisonings, psychological distresses, chemicals, infections, inflammation, autoimmune diseases, degenerative processes, hypoxia, ischemia, metabolic derangements and cancer/radiation.

BACKGROUND OF THE INVENTION

Acquired brain injury (ABI) and Acquired Spinal Cord Injury (ASI) are brain and spinal damage, respectively, caused by events that occur in utero, perinatal and post-natal. These impairments result from either traumatic brain injury (e.g. mechanical, pressure-wave, etc.) or non-traumatic injury derived from either an internal or external source (e.g. stroke, tumors, infection, poisoning, hypoxia, ischemia, radiation, substance abuse, etc.).

Traumatic brain injury (TBI) is an insult to the brain from an external mechanical force, leading to permanent or temporary impairment of cognitive, physical, and psychosocial functions, with an associated diminished or altered state of consciousness (includes both concussion and blast injury). The Head Injury Interdisciplinary Special Interest Group of the American Congress of Rehabilitation Medicine defines "mild" TBI as "a traumatically induced physiologic disruption of brain function, as manifested by one of the following: any period of loss of consciousness (LOC), any loss of memory for events immediately before or after the event, any alteration in mental state at the time of the event and focal neurologic deficits, which may or may not be transient. The Glasgow Coma Scale (GCS) helps defines the severity of a TBI (3-8, severe; 9-12 moderate; 13-15 mild), based on eye, verbal and motor responses. TBI is a major public health concern of epidemic proportions, with an annual incidence of 1.6 to 3.2 million in the United States. Mild TBI or mTBI, of which concussion and blast wave injury are subsets, is the most common form, representing nearly 75% of all TBIs [www.cdc.gov/]. Mild TBI may be caused by impact forces in which the head strikes or is struck by something, o impulsive forces, in which the head moves without itself being subject to trauma (for example, when the chest hits something and the head snaps forward). All age groups suffer concussions, from the very young to the elderly. Certain activities are more frequently associated with concussions, including athletics and military service, but they also result from general trauma caused by motor vehicle collisions, falls from height and assaults. Concussions often result in significant acute symptoms and in some individuals, long-term neurological dysfunction.

A pressure-wave (e.g., bomb blast) may cause the full severity range of TBI, from mild to severe, and may include penetrating injury from projectiles. The pathophysiology of blast-related TBI is distinctive, with injury magnitude dependent on several factors, including blast energy and distance from the blast epicenter (Rosenfeld, et al., Lancet Neurol. 2013 September; 12(9):882-93.). A blast injury is a complex type of physical trauma resulting from direct or indirect exposure to an explosion. (Rosenfeld, et al., Lancet Neurol. 2013 September; 12(9):882-93.) Primary injuries are caused by blast overpressure waves, or shock waves. These are especially likely when a person is close to an exploding munition, such as a land mine. Animal models suggest that the brain is vulnerable to primary blast injury. Shear and stress waves from the over-pressurization could potentially cause TBI directly (e.g., concussion, hemorrhage, edema, diffuse axonal injury). The primary blast mechanism can also result in cerebral infarction due to blast lung injury and consequent formation of gas emboli. ["Blast Injuries: Traumatic Brain Injuries from Explosions", Brainline.org]

While diagnosis of moderate to severe TBI is straightforward, mild TBI is under-diagnosed following concussion and explosive events. ["Blast Injuries: Traumatic Brain Injuries from Explosions", Brainline.org] That is, while moderate and severe TBI are easily diagnosed based on clinical signs, mild TBI can be missed due to subtle, transient or absent clinical signs. The latter require an objective diagnostic, such as a blood test that is sensitive, specific and reproducible.

Diagnosis of clinically significant mTBI can be difficult, as are the decisions to stop play or activities. It is also unclear when mTBI patients should return to daily activities. Thus, there is great interest in discovery of biomarkers to aid in mTBI, including primary brain blast injury and concussion diagnoses, prognoses and rehabilitation. At present, no single biomarker has sufficient sensitivity and specificity.

Non-traumatic brain injuries (non-TBI) can also result in mildly abnormal neurological symptoms. Given the often subtle nature of non-TBI injuries, they could be better identified with an objective diagnostic test, such as a blood test, that is sensitive, specific and reproducible.

Traumatic spinal cord injuries (TSI; e.g injuries from spine hyperflexion, hyperextension, lateral stress, rotation, compression, distraction and partial spinal cord transection; often from motor vehicle collisions, falls from height, sports, etc.) and non-traumatic spinal cord injuries (non-TSI; e.g, intervertebral disk disease, interruption of blood supply, infection, electrocution, cancer, radiation, etc) can also result in mild peripheral symptoms (e.g., an "incomplete" injury). Given the often subtle nature of TSI and non-TSI injuries, they could be better identified with an objective diagnostic test, such as a blood test, that is sensitive, specific and reproducible.

Metabolomics is relatively new field of study that measures a person's small metabolite profile (<1500 Daltons). Two common methods for metabolomics are nuclear magnetic resonance (NMR) spectroscopy and mass spectrometry (MS). The former measures a large number of metabolites, but lacks sensitivity (micromolar range), while the latter is very sensitive for quantifying amino acids, acylcarnitines, glycerophospholipids, sphingolipids and sugars (picomolar range). The allure of metabolomics lies with the concept that metabolites fall downstream of genetic, transcriptomic, proteomic, and environmental variation, thus providing the most integrated and dynamic measure of phenotype and medical condition.

SUMMARY OF THE INVENTION

The present invention relates to the use metabolomic profiling or individual metabolites as biomarkers to diagnose central nervous system (CNS) injuries, including acquired brain injury (ABI) and acquired spinal injury (ASI). These injuries can be traumatic (mTBI and mTSI) and non-traumatic (non-TBI and non-TSI) including concussion or contusion, blast injury, as well as stroke, poisoning, psychological distress, chemical, infection, inflammation, autoimmune, degenerative, hypoxic, ischemic, metabolic and cancer/radiation-induced brain/spinal injuries. The present invention relates to the use metabolomic profiling or individual metabolites as biomarkers to specifically diagnose brain and/or spinal cord injuries. Solely for the purpose of this document, the term "ACNSI" (acquired CNS injury) will be used to mean "ABI and/or ASI". Also, non-CNSI (non-CNS injury) will be used to mean normal or control subject.

In one embodiment, the present invention is a method of diagnosing ACNSI in a subject including: (a) obtaining a metabolite profile from the subject; and (b) using multivariate statistical analysis and machine learning to compare the subject's profile with a predetermined set of metabolite profiles of ACNSI and a predetermined set of metabolite profiles of non-CNSI to diagnose if the subject has ACNSI.

In one embodiment of the method of diagnosing ACNSI, the predetermined set of ACNSI and non-ACNSI metabolite profiles are obtained by obtaining a first metabolite profile from a population of subjects known to have ACNSI and a second metabolite profile from a population of control non-ACNSI (referred to as "normal") subjects.

In another embodiment of the method of diagnosing ACNSI, the metabolite profile of the subject and the first and second predetermined sets of ACNSI and non-ACNSI profiles are provided as sets of multi-dimensional metabolomics data, and wherein step (b) comprises applying to the sets of multi-dimensional metabolomics data (i) a dimensionality reduction, (ii) a feature selection, or (iii) both dimensionality reduction and feature selection, to obtain a reduced metabolomics data set.

In another embodiment of the method of diagnosing ACNSI, step (b) comprises normalizing the set metabolite profile of the subject and the sets of predetermined metabolite profiles of ACNSI and non-ACNSI to obtain matrix, and performing principal components analysis directly on the metabolite matrix.

In another embodiment, the present invention is a method of diagnosing ACNSI in a subject including: (a) obtaining a metabolite profile from the subject; (b) creating a matrix of pairwise correlations between the metabolite profile of the subject and a predetermined set of ACNSI profiles and a predetermined set of non-ACNSI profiles and identifying ACNSI and non-ACNSI clusters in the correlation matrix; and (c) determining if the subject's profile falls within the ACNSI cluster or the non-ACNSI cluster.

In one embodiment of the previous method of diagnosing ACNSI in a subject, the predetermined ACNSI and non-ACNSI sets of metabolite profiles are obtained respectively by obtaining a first set of metabolite profiles from a population of subjects known to have ACNSI and a second set of metabolite profiles from a population of control non-ACNSI (normal) subjects.

In another embodiment, the present invention is a method of tracking or following the efficiency of a medical intervention (including rehabilitation therapy) in an ACNSI patient, the method including: (a) obtaining metabolite profiles from the patient at different times during the medical intervention (rehabilitation therapy); and (b) using multivariate statistical analysis and machine learning to compare the patient's profiles at each of the different times with a predetermined set of metabolite profiles of ACNSI and a predetermined set of metabolite profiles of non-ACNSI to follow the efficiency of the medical intervention (rehabilitation therapy) in the patient.

In one embodiment of the method of tracking the efficiency of a medical intervention (including rehabilitation therapy) in an ACNSI patient of the present invention, the predetermined set of ACNSI and non-ACNSI metabolite profiles are obtained by obtaining a first metabolite profile from a population of subjects known to have ACNSI and a second metabolite profile from a population of control non-ACNSI (referred to as "normal") subjects.

In another embodiment of the method of tracking the efficiency of a medical intervention (including rehabilitation therapy) in an ACNSI patient of the present invention, the metabolite profiles of the patient and the first and second predetermined sets of ACNSI and non-ACNSI metabolite profiles are provided as sets of multi-dimensional metabolomics data, and wherein step (b) comprises applying to the sets of multi-dimensional metabolomics data (i) a dimensionality reduction, (ii) a feature selection, or (iii) both dimensionality reduction and feature selection, to obtain a reduced metabolomics data set.

In another embodiment of the method of tracking or following the efficiency of a medical intervention (including rehabilitation therapy) in an ACNSI patient of the present invention, step (b) comprises normalizing the metabolite profiles of the patient and the sets of predetermined metabolite profiles of ACNSI and non-ACNSI to obtain matrix, and performing principal components analysis directly on the metabolite matrix.

In another embodiment of the method of tracking the efficiency of a medical intervention (including rehabilitation therapy) in an ACNSI patient of the present invention, the predetermined set of metabolite profiles of ACNSI and non-ACNSI are matched for one or more of: age, sex, activity, body habitus, nutrition, medications and morbidity.

In another embodiment of the method of tracking the efficiency of a medical intervention (including rehabilitation therapy) in an ACNSI patient of the present invention, the patient's metabolite profile and the predetermined set of metabolite profiles are obtained using metabolomics.

In another embodiment of the method of tracking the efficiency of a medical intervention (including rehabilitation therapy) in an ACNSI patient of the present invention, the metabolomics is performed with one or more of high performance liquid chromatography, thin layer chromatography, electrochemical analysis, mass spectroscopy (MS), refractive index spectroscopy, ultra-violet spectroscopy, fluorescent analysis, radiochemical analysis, near-infrared spectroscopy, nuclear magnetic resonance (NMR), light scattering analysis, gas chromatography (GC), or GC coupled with MS, direct injection (DI) coupled with LC-MS/MS.

In another embodiment of the method of tracking the efficiency of a medical intervention (including rehabilitation therapy) in an ACNSI patient of the present invention, the obtaining, using, creating and determining steps are executed using a suitably programmed computer.

In one embodiment of the method according to any one of the previous embodiment, the predetermined profile of ACNSI and non-ACNSI are matched for one or more of: age, sex, activity, nutrition, body habitus, medications and co-morbidity.

In another embodiment of the methods according to any one of the previous embodiment, the subject's/patient's metabolite (including lipids and fatty acids) profile and the predetermined set of metabolite profiles are obtained using metabolomics.

In another embodiment of the methods according to any one of the previous embodiment, the metabolomics (including lipids and fatty acids) is performed with one or more of high performance liquid chromatography, thin layer chromatography, electrochemical analysis, mass spectroscopy (MS), refractive index spectroscopy, ultra-violet spectroscopy, fluorescent analysis, radiochemical analysis, near-infrared spectroscopy, nuclear magnetic resonance (NMR), light scattering analysis, gas chromatography (GC), or GC coupled with MS, direct injection (DI) coupled with LC-MS/MS.

In another embodiment of the methods according to any one of the previous embodiment, the obtaining, using, creating and determining steps are executed using a suitably programmed computer.

In another embodiment of the methods according to any one of the previous embodiment, the metabolite profiles are obtained from a biological test sample selected from the group consisting of: blood, blood plasma, blood serum, saliva, synovial fluid, urine, spinal fluid, bronchoalveolar lavage and extracts. In one aspect, the metabolite includes phospholipids, glycerophospholipids, lipids, plasmalogens, fatty acids, sugars, amino acids, nucleotides, intermediates formed during cellular processes, or combinations thereof. In another aspect, the metabolite includes lipids and fatty acids or combinations thereof.

In another embodiment of the methods according to any one of the previous embodiment, the metabolite profiles include the following metabolites: C5, PC aa C32:1, PC aa C32:2, PC aa C36:5, PC aa C36:6, PC ae C34:0, PC ae C34:3, PC ae C36:0, PC ae C36:1, PC ae C36:2, PC ae C38:1, PC ae C38:2, PC ae C38:3, Putrescine, Formate, Methanol, and Succinate.

In another embodiment of the methods according to any one of the previous embodiment, the metabolite profiles include the following metabolites: C5, PC aa C30:2, PC aa C32:0, PC aa C32:1, PC aa C32:2, PC aa C32:3, PC aa C34:4, PC aa C36:6, PC aa C42:6, PC ae C30:0, PC ae C30:1, PC ae C32:1, PC ae C34:0, PC ae C34:2, PC ae C34:3, PC ae C36:0, PC ae C36:2, PC ae C38:1, PC ae C38:3, SM C22:3, SM C24:0, SM C24:1, alpha-Aminoadipic acid, trans-OH-Proline, Putrescine, Betaine, Formate, Glucose, Glycerol, Methanol, and Serine.

In another embodiment of the methods according to any of the previous embodiments of the present invention, the ACNSI is selected from mTSI and non-TSI. In one aspect of this embodiment, the mTSI includes spinal cord contusion, stretch and/or partial transection, and the non-TSI includes injuries caused by intervertebral disk disease, electricity, stroke, poisoning, chemical, infectious, ischemia, metabolic, inflammatory, autoimmune, degenerative, hypoxic, and cancer/radiation-induced spinal cord injuries.

In another embodiment of the methods according to any of the previous embodiments of the present invention, the ACNSI is selected from mTBI and non-TBI.

In another embodiment of the methods according to any one of the previous embodiment, the ACNSI is mTBI. In one aspect of this embodiment the mTBI is concussion or primary blast in blast-induced traumatic brain injury.

In another embodiment of the methods according to any of the previous embodiments of the present invention, the ACNSI is non-TBI. In one aspect of this embodiment, the non-TBI is selected from electrical-induced brain injury (electrocution), seizure-induced brain injury, surgical-induced brain injury, stroke-induced brain injury, poison-induced brain injury, psychological brain injury, chemical brain injury, infectious brain injury, ischemic brain injury, metabolic brain injury, inflammatory brain injury, autoimmune brain injury, degenerative brain injury, hypoxic brain injury, and cancer/radiation-induced brain injury.

In another embodiment of the methods according to any one of the previous embodiment, the ACNSI is concussion.

In another embodiment of the methods according to any one of the previous embodiment, the ACNSI is primary blast in blast-induced traumatic brain injury.

In another embodiment, the present invention is a computer program product for use in conjunction with a computer system, the computer program product including a non-transitory computer readable storage medium and a computer program mechanism embedded therein, the computer program mechanism comprising executable instructions for performing a method of diagnosing ACNSI in a subject, said executable instructions comprising: (a) using multivariate statistical analysis and machine learning to compare a subject's metabolic profile with a predetermined set of ACNSI metabolic profiles and a predetermined set of normal metabolic profiles; and (b) determining if the subject has ACNSI based on said comparison.

In one embodiment of the computer program product of the present invention, the program mechanism further comprises executable instructions for: (i) identifying metabolites in a first set of biological samples from a population of subjects known to have ACNSI and in a second set of biological samples from a population of control non-ACNSI (referred to as "normal") subjects thereby obtaining the predetermined ACNSI profile and the predetermined normal profile using the ACNSI and normal metabolite matrices.

In another embodiment of the computer program product of the present invention, an initial dimensionality reduction is performed on the subject's metabolite profile and in the predetermined ACNSI and normal profiles by t-SNE.

In another embodiment of the computer program product according to any of the previous embodiments of the present invention, the ACNSI is selected from mTSI and non-TSI. In one aspect of this embodiment, the mTSI includes spinal cord contusion, stretch and/or partial transection, and the non-TSI includes injuries caused by intervertebral disk disease, electricity, stroke, poisoning, chemical, infectious, ischemia, metabolic, inflammatory, autoimmune, degenerative, hypoxic, and cancer/radiation-induced spinal cord injuries.

In another embodiment of the computer program product according to any of the previous embodiments of the present invention, the ACNSI is selected from mTBI and non-TBI.

In another embodiment of the computer program product according to any of the previous embodiments of the present invention, the ACNSI is mTBI. In one aspect of this embodiment the mTBI is concussion or primary blast in blast-induced traumatic brain injury.

In another embodiment of the computer program product according to any of the previous embodiments of the present invention, the ACNSI is non-TBI. In one aspect of this embodiment, the non-TBI is selected from electrical-induced brain injury (electrocution), seizure-induced brain injury, surgical-induced brain injury, stroke-induced brain injury, poison-induced brain injury, psychological brain injury, chemical brain injury, infectious brain injury, ischemic brain injury, metabolic brain injury, inflammatory brain injury, autoimmune brain injury, degenerative brain injury, hypoxic brain injury, and cancer/radiation-induced brain injury.

In another embodiment, the present invention provides for a method of assessing a non-human animal model of human ACNSI, the method including: (a) obtaining a metabolite profile from the non-human animal model of ACNSI; and (b) using multivariate statistical analysis and machine learning to compare the non-human animal model profile with a predetermined set of metabolite profiles of human ACNSI and a predetermined set of metabolite profiles of human non-ACNSI to determine if the non-human animal classifies as ACNSI.

In one embodiment of the method of assessing a non-human animal model of ACNSI, the predetermined sets of human ACNSI and non-ACNSI metabolite profiles are obtained by obtaining a first metabolite profile from a population of subjects known to have ACNSI and a second metabolite profile from a population of control non-ACNSI (referred to as "normal") subjects.

In another embodiment of the method of assessing a non-human animal model of ACNSI, the metabolite profile of the non-human animal model of ACNSI and the first and second predetermined sets of ACNSI and non-ACNSI profiles are provided as sets of multi-dimensional metabolomics data, and wherein step (b) comprises applying to the sets of multi-dimensional metabolomics data (i) a dimensionality reduction, (ii) a feature selection, or (iii) both dimensionality reduction and feature selection, to obtain a reduced metabolomics data set.

In another embodiment of the method of assessing a non-human animal model of ACNSI, step (b) comprises normalizing the set metabolite profile of the non-human animal and the sets of predetermined metabolite profiles of ACNSI and non-ACNSI to obtain matrix, and performing principal components analysis directly on the metabolite matrix.

In another embodiment of assessing a non-human animal model of ACNSI according to any of the previous embodiments of the present invention, the ACNSI is selected from mTSI and non-TSI. In one aspect of this embodiment, the mTSI includes spinal cord contusion, stretch and/or partial transection, and the non-traumatic spinal cord injuries includes injuries caused by intervertebral disk disease, electricity, stroke, poisoning, chemical, infectious, ischemia, metabolic, inflammatory, autoimmune, degenerative, hypoxic, and cancer/radiation-induced spinal cord injuries.

In another embodiment of the method of assessing a non-human animal model of ACNSI according to any of the previous embodiments of the present invention, the ACNSI is selected from mTBI and non-TBI.

In another embodiment of the method of assessing a non-human animal model of ACNSI according to any of the previous embodiments of the present invention, the ACNSI is mTBI. In one aspect of this embodiment the mTBI is concussion or primary blast in blast-induced traumatic brain injury In another embodiment of the method of assessing a non-human animal model of ACNSI according to any of the previous embodiments of the present invention, the ACNSI is non-TBI. In one aspect of this embodiment, the non-TBI is selected from stroke-induced brain injury, poison-induced brain injury, psychological brain injury, chemical brain injury, infectious brain injury, ischemic brain injury, metabolic brain injury, inflammatory brain injury, autoimmune brain injury, degenerative brain injury, hypoxic brain injury, and cancer/radiation-induced brain injury.

BRIEF DESCRIPTION OF THE DRAWINGS

The following figures illustrate various aspects and preferred and alternative embodiments of the invention.

DESCRIPTION OF THE INVENTION

Abbreviations

Figure 1:
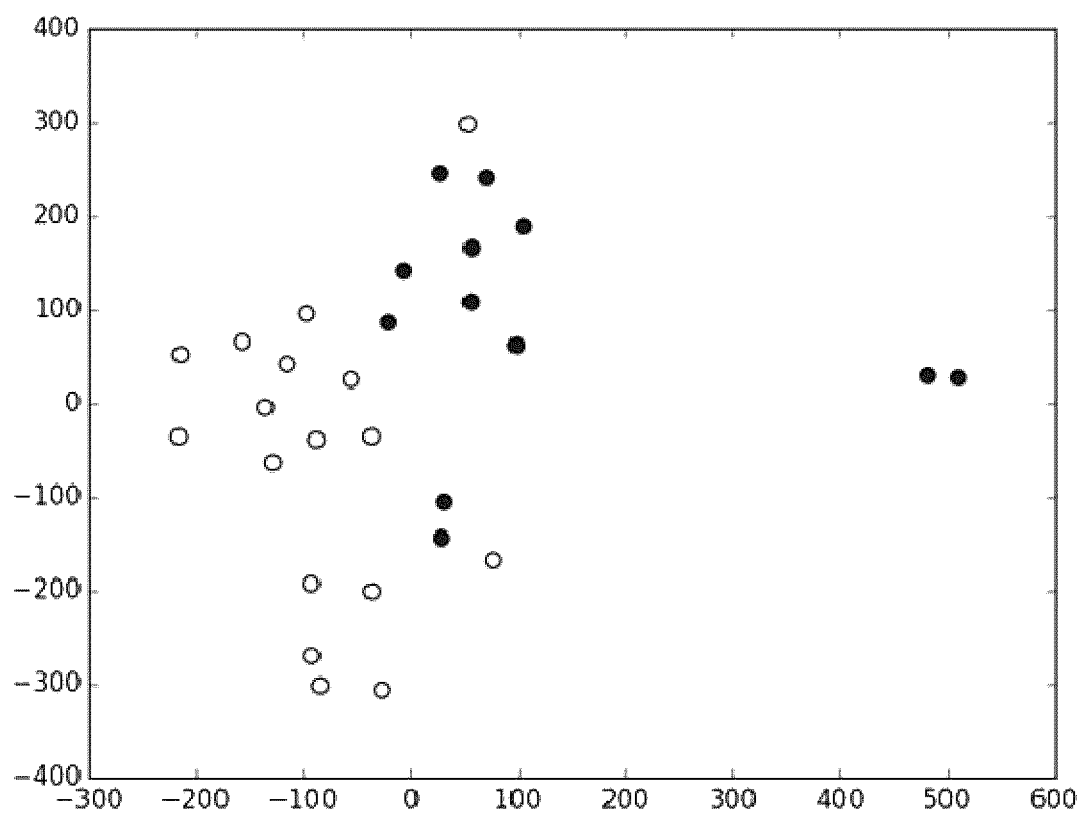
FIG. 1: Graph of individual subjects plotted in the reduced 2-dimensional space to illustrate the power of the t-SNE dimensionality reduction step (12 concussed subjects—filled circles, 17 control subjects—open circles).

| Table of MS Metabolites | |
|---|---|
| C0 (Carnitine) | Acylcarnitines |
| C10 (Decanoylcarnitine) | Acylcarnitines |
| C10:1 (Decenoylcarnitine) | Acylcarnitines |
| C10:2 (Decadienylcarnitine) | Acylcarnitines |
| C12 (Dodecanoylcarnitine) | Acylcarnitines |
| C12-DC (Dodecanedioylcarnitine) | Acylcarnitines |
| C12:1 (Dodecenoylcarnitine) | Acylcarnitines |
| C14 (Tetradecanoylcarnitine) | Acylcarnitines |
| C14:1 (Tetradecenoyl carnitine) | Acylcarnitines |
| C14:1-OH (Hydroxytetradecenoyl carnitine) | Acylcarnitines |
| C14:2 (Tetradecadienylcarnitine) | Acylcarnitines |
| C14:2-OH (Hydroxytetradecadienylcarnitine) | Acylcarnitines |
| C16 (Hexadecanoylcarnitine) | Acylcarnitines |
| C16-OH (Hydroxyhexadecanoylcarnitine) | Acylcarnitines |
| C16:1 (Hexadecenoylcarnitine) | Acylcarnitines |
| C16:1-OH (Hydroxyhexadecenoylcarnitine) | Acylcarnitines |
| C16:2 (Hexadecadienylcarnitine) | Acylcarnitines |
| C16:2-OH (Hydroxyhexadecadienylcarnitine) | Acylcarnitines |
| C18 (Octadecanoylcarnitine) | Acylcarnitines |

Table of MS Metabolites

| | |
|---|---|
| C18:1 (Octadecenoylcarnitine) | Acylcarnitines |
| C18:1-OH (Hydroxyoctadecenoylcarnitine) | Acylcarnitines |
| C18:2 (Octadecadienylcarnitine) | Acylcarnitines |
| C2 (Acetylcarnitine) | Acylcarnitines |
| C3 (Propionylcarnitine) | Acylcarnitines |
| C3-OH (Hydroxypropionylcarnitine) | Acylcarnitines |
| C3:1 (Propenoylcarnitine) | Acylcarnitines |
| C4 (Butyrylcarnitine) | Acylcarnitines |
| C4-OH (C3-DC) (Hydroxybutyrylcarnitine) | Acylcarnitines |
| C4:1 (Butenylcarnitine) | Acylcarnitines |
| C5 (Valerylcarnitine) | Acylcarnitines |
| C5-DC (C6-OH)(Glutarylcarnitine) | Acylcarnitines |
| C5-M-DC (Methylglutarylcarnitine) | Acylcarnitines |
| C5-OH (C3-DC-M) (Hydroxyvalerylcarnitine) | Acylcarnitines |
| C5:1 (Tiglylcarnitine) | Acylcarnitines |
| C5:1-DC (Glutaconylcarnitine) | Acylcarnitines |
| C6 (C4:1-DC) (Hexanoylcarnitine) | Acylcarnitines |
| C6:1 (Hexenoylcarnitine) | Acylcarnitines |
| C7-DC (Pimelylcarnitine) | Acylcarnitines |
| C8 (Octanoylcarnitine) | Acylcarnitines |
| C9 (Nonaylcarnitine) | Acylcarnitines |
| Alanine | Amino Acids |
| Arginine | Amino Acids |
| Asparagine | Amino Acids |
| Aspartate | Amino Acids |
| Citrulline | Amino Acids |
| Glutamate | Amino Acids |
| Glutamine | Amino Acids |
| Glycine | Amino Acids |
| Histidine | Amino Acids |
| Isoleucine | Amino Acids |
| Leucine | Amino Acids |
| Lysine | Amino Acids |
| Methionine | Amino Acids |
| Ornithine | Amino Acids |
| Phenylalanine | Amino Acids |
| Proline | Amino Acids |
| Serine | Amino Acids |
| Threonine | Amino Acids |
| Tryptophan | Amino Acids |
| Tyrosine | Amino Acids |
| Valine | Amino Acids |
| Acetylornithine | Biogenic amines |
| Aminoadipic acid | Biogenic amines |
| Asymmetric dimethylarginine | Biogenic amines |
| Carnosine | Biogenic amines |
| Creatinine | Biogenic amines |
| Dopa | Biogenic amines |
| Dopamine | Biogenic amines |
| Histamine | Biogenic amines |
| Hydroxyproline | Biogenic amines |
| Kynurenine | Biogenic amines |
| Methionine sulfoxide | Biogenic amines |
| Nitrotyrosine | Biogenic amines |
| Phenylethylamine | Biogenic amines |
| Putrescine | Biogenic amines |
| Sarcosine | Biogenic amines |
| Serotonin | Biogenic amines |
| Spermidine | Biogenic amines |
| Spermine | Biogenic amines |
| Symmetric dimethylarginine | Biogenic amines |
| Taurine | Biogenic amines |
| Total dimethylarginine | Biogenic amines |
| Hexose | Carbohydrates |
| lysoPC a C14:0 | Phospholipids |
| lysoPC a C16:0 | Phospholipids |
| lysoPC a C16:1 | Phospholipids |
| lysoPC a C17:0 | Phospholipids |
| lysoPC a C18:0 | Phospholipids |
| lysoPC a C18:1 | Phospholipids |
| lysoPC a C18:2 | Phospholipids |
| lysoPC a C20:3 | Phospholipids |
| lysoPC a C20:4 | Phospholipids |
| lysoPC a C24:0 | Phospholipids |
| lysoPC a C26:0 | Phospholipids |
| lysoPC a C26:1 | Phospholipids |
| lysoPC a C28:0 | Phospholipids |
| lysoPC a C28:1 | Phospholipids |
| PC aa C24:0 | Phospholipids |
| PC aa C26:0 | Phospholipids |
| PC aa C28:1 | Phospholipids |
| PC aa C30:0 | Phospholipids |
| PC aa C30:2 | Phospholipids |
| PC aa C32:0 | Phospholipids |
| PC aa C32:1 | Phospholipids |
| PC aa C32:2 | Phospholipids |
| PC aa C32:3 | Phospholipids |
| PC aa C34:1 | Phospholipids |
| PC aa C34:2 | Phospholipids |
| PC aa C34:3 | Phospholipids |
| PC aa C34:4 | Phospholipids |
| PC aa C36:0 | Phospholipids |
| PC aa C36:1 | Phospholipids |
| PC aa C36:2 | Phospholipids |
| PC aa C36:3 | Phospholipids |
| PC aa C36:4 | Phospholipids |
| PC aa C36:5 | Phospholipids |
| PC aa C36:6 | Phospholipids |
| PC aa C38:0 | Phospholipids |
| PC aa C38:1 | Phospholipids |
| PC aa C38:3 | Phospholipids |
| PC aa C38:4 | Phospholipids |
| PC aa C38:5 | Phospholipids |
| PC aa C38:6 | Phospholipids |
| PC aa C40:1 | Phospholipids |
| PC aa C40:2 | Phospholipids |
| PC aa C40:3 | Phospholipids |
| PC aa C40:4 | Phospholipids |
| PC aa C40:5 | Phospholipids |
| PC aa C40:6 | Phospholipids |
| PC aa C42:0 | Phospholipids |
| PC aa C42:1 | Phospholipids |
| PC aa C42:2 | Phospholipids |
| PC aa C42:4 | Phospholipids |
| PC aa C42:5 | Phospholipids |
| PC aa C42:6 | Phospholipids |
| PC ae C30:0 | Phospholipids |
| PC ae C30:1 | Phospholipids |
| PC ae C32:1 | Phospholipids |
| PC ae C32:2 | Phospholipids |
| PC ae C34:0 | Phospholipids |
| PC ae C34:1 | Phospholipids |
| PC ae C34:2 | Phospholipids |
| PC ae C34:3 | Phospholipids |
| PC ae C36:0 | Phospholipids |
| PC ae C36:1 | Phospholipids |
| PC ae C36:2 | Phospholipids |
| PC ae C36:3 | Phospholipids |
| PC ae C36:4 | Phospholipids |
| PC ae C36:5 | Phospholipids |
| PC ae C38:0 | Phospholipids |
| PC ae C38:1 | Phospholipids |
| PC ae C38:2 | Phospholipids |
| PC ae C38:3 | Phospholipids |
| PC ae C38:4 | Phospholipids |
| PC ae C38:5 | Phospholipids |
| PC ae C38:6 | Phospholipids |
| PC ae C40:1 | Phospholipids |
| PC ae C40:2 | Phospholipids |
| PC ae C40:3 | Phospholipids |
| PC ae C40:4 | Phospholipids |
| PC ae C40:5 | Phospholipids |
| PC ae C40:6 | Phospholipids |
| PC ae C42:0 | Phospholipids |
| PC ae C42:1 | Phospholipids |
| PC ae C42:2 | Phospholipids |
| PC ae C42:3 | Phospholipids |
| PC ae C42:4 | Phospholipids |
| PC ae C42:5 | Phospholipids |
| PC ae C44:3 | Phospholipids |
| PC ae C44:4 | Phospholipids |
| PC ae C44:5 | Phospholipids |
| PC ae C44:6 | Phospholipids |
| SM (OH) C14:1 | Sphingolipids |

-continued

Table of MS Metabolites

| | |
|---|---|
| SM (OH) C16:1 | Sphingolipids |
| SM (OH) C22:1 | Sphingolipids |
| SM (OH) C22:2 | Sphingolipids |
| SM (OH) C24:1 | Sphingolipids |
| SM C16:0 | Sphingolipids |
| SM C16:1 | Sphingolipids |
| SM C18:0 | Sphingolipids |
| SM C18:1 | Sphingolipids |
| SM C20:2 | Sphingolipids |
| SM C22:3 | Sphingolipids |
| SM C24:0 | Sphingolipids |
| SM C24:1 | Sphingolipids |
| SM C26:0 | Sphingolipids |
| SM C26:1 | Sphingolipids |

Definitions

Unless defined otherwise, all technical and scientific terms used herein have the same meaning as commonly understood by one of ordinary skill in the art to which this invention belongs. Also, unless indicated otherwise, except within the claims, the use of "or" includes "and" and vice versa. Non-limiting terms are not to be construed as limiting unless expressly stated or the context clearly indicates otherwise (for example "including", "having" and "comprising" typically indicate "including without limitation"). Singular forms including in the claims such as "a", "an" and "the" include the plural reference unless expressly stated otherwise. In order to aid in the understanding and preparation of the within invention, the following illustrative, non-limiting, examples are provided.

In this document the definition of "mild traumatic brain injury" "mTBI", which may also be referred to in the literature as mild head injury or concussion, is that taken from the American Congress of Rehabilitation Medicine (ACRM; J Head Trauma Rehabil 1993; 8(3):86-87), and it refers to a person who has had a traumatically induced physiological disruption of brain function, as manifested by at least one of the following: 1. any period of loss of consciousness; 2. any loss of memory for events immediately before or after the event; 3. any alteration in mental state at the time of the event (eg, feeling dazed, disoriented, or confused); and 4. focal neurological deficit(s) that may or may not be transient; but where the severity of the injury does not exceed the following: loss of consciousness of approximately 30 minutes or less; after 30 minutes, an initial Glasgow Coma Scale (GCS) of 13-15; and posttraumatic amnesia (PTA) not greater than 24 hours. This definition includes: 1. the head being struck, 2. the head striking an object, and 3. the brain undergoing an acceleration/deceleration movement (ie, whiplash) without direct external trauma to the head. Computed tomography, magnetic resonance imaging, electroencephalogram, near infrared spectroscopy, positive emission tomography or routine neurological evaluations may be normal. Due to the lack of medical emergency, or the realities of certain medical systems, some patients may not have the above factors medically documented in the acute stage. In such cases, it is appropriate to consider symptomotology that, when linked to a traumatic head injury, can suggest the existence of a mTBI.

"Non-traumatic brain injuries" (non-TBI) include brain injuries that may be the result of strokes, poisonings, psychological distresses, chemicals, infections, inflammation, autoimmune diseases, degenerative processes, hypoxia, ischemia, metabolic derangements and cancer/radiation.

In this document the definition of "mild traumatic spinal cord injury" "mTSI" is an incomplete injury with one or more spinal symptoms that may resolve over time (e.g. loss of bowel or bladder control, poor regulation of blood pressure and body temperature, pain, poor sensation, poor sense of body position, sexual dysfunction, etc.). Causes of mTSI may include contusion, stretch and partial cord transection.

"Non-traumatic spinal cord injuries" (non-TSI) include spinal cord injuries that may be the result of strokes, poisonings, chemicals, infections, inflammation, autoimmune diseases, degenerative processes, hypoxia, ischemia, metabolic derangements and cancer/radiation.

"Metabolome" refers to the collection of all metabolites in a biological cell, tissue, organ or organism, which are the end products of cellular processes. "Metabolome" includes lipidome, sugars, nucleotides and amino acids. Lipidome is the complete lipid profile in a biological cell, tissue, organ or organism.

"Metabolomic profiling" refers to the characterization and/or measurement of the small molecule metabolites in biological specimen or sample, including cells, tissue, organs, organisms, or any derivative fraction thereof and fluids such as blood, blood plasma, blood serum, saliva, synovial fluid, spinal fluids, urine, bronchoalveolar lavage, tissue extracts and so forth.

The metabolite profile may include information such as the quantity and/or type of small molecules present in the sample. The ordinarily skilled artisan would know that the information which is necessary and/or sufficient will vary depending on the intended use of the "metabolite profile." For example, the "metabolite profile," can be determined using a single technique for an intended use but may require the use of several different techniques for another intended use depending on such factors as the disease state involved, the types of small molecules present in a particular targeted cellular compartment, the cellular compartment being assayed per se., and so forth.

The relevant information in a "metabolite profile" may also vary depending on the intended use of the compiled information, e.g. spectrum. For example for some intended uses, the amounts of a particular metabolite or a particular class of metabolite may be relevant, but for other uses the distribution of types of metabolites may be relevant.

Metabolite profiles may be generated by several methods, e.g., HPLC, thin layer chromatography (TLC), electrochemical analysis, Mass Spectroscopy (MS), refractive index spectroscopy (RI), Ultra-Violet spectroscopy (UV), fluorescent analysis, radiochemical analysis, Near-InfraRed spectroscopy (Near-IR), Nuclear Magnetic Resonance spectroscopy (NMR), fluorescence spectroscopy, dual polarisation interferometry, computational methods, Light Scattering analysis (LS), gas chromatography (GC), or GC coupled with MS, direct injection (DI) coupled with LC-MS/MS and/or other methods or combination of methods known in the art.

The term "small molecule metabolites" includes organic and inorganic molecules which are present in the cell, cellular compartment, or organelle, usually having a molecular weight under 2,000, or 1,500. The term does not include large macromolecules, such as large proteins (e.g., proteins with molecular weights over 2,000, 3,000, 4,000, 5,000, 6,000, 7,000, 8,000, 9,000, or 10,000), large nucleic acids (e.g., nucleic acids with molecular weights of over 2,000, 3,000, 4,000, 5,000, 6,000, 7,000, 8,000, 9,000, or 10,000), or large polysaccharides (e.g., polysaccharides with a molecular weights of over 2,000, 3,000, 4,000, 5,000, 6,000, 7,000, 8,000, 9,000, or 10,000). The small molecule metabolites of the cell are generally found free in solution in the cytoplasm or in other organelles, such as the mitochondria, where they form a pool of intermediates which can be metabolized further or used to generate large molecules, called macromolecules. The term "small molecule metabolites" includes signaling molecules and intermediates in the chemical reactions that transform energy derived from food into usable forms. Examples of small molecule metabolites include phospholipids, glycerophospholipids, lipids, plasmalogens, sugars, fatty acids, amino acids, nucleotides, intermediates formed during cellular processes, isomers and other small molecules found within the cell. In one embodiment, the small molecules of the invention are isolated. Preferred metabolites include lipids and fatty acids.

The term "subject" as used herein refers all members of the animal kingdom including mammals, preferably humans.

The term "patient" as used herein refers to a subject that is suspected of having an acquired injury of the central nervous system (ACNSI). In this document ACNSI includes an acquired brain injury (ABI) and an acquired spinal cord injury (ASI). These injuries may be traumatic (mTBI and mTSI) and non-traumatic (non-TBI and non-TSI). mTBI includes concussion and blast, including blast overpressure wave injury. Non-TBI includes electrical-induced brain injury (electrocution), seizure-induced brain injury, surgical-induced brain injury, stroke-induced brain injury, poison-induced brain injury, psychological brain injury, chemical brain injury, infectious brain injury, ischemic brain injury, metabolic brain injury, inflammatory brain injury, autoimmune brain injury, degenerative brain injury, hypoxic brain injury, and cancer/radiation-induced brain injury. mTSI includes spinal cord contusion, stretch and/or partial transection, and the non-TSI includes intervertebral disk disease, electrical, stroke, poisoning, chemical, infectious, ischemia, metabolic, inflammatory, autoimmune, degenerative, hypoxic, and cancer/radiation-induced spinal cord injuries.

Overview

The present invention relates to the use metabolomic profiling in diagnosing acquired central nervous system injuries (ACNSI), including ABI and ASI. ABI includes mTBI and non-TBI. ASI includes mTSI and non-TSI. Traumatic injuries to the brain and spinal cord may include concussion and blast, including blast overpressure wave injury as well as spinal cord contusion, stretch and/or partial transection. Non-traumatic injuries (non-TBI and non-TSI) may include electrical-induced (electrocution), seizure-induced, surgical-induced, strokes, poisonings, psychological distresses, chemicals, infections, inflammation, autoimmune diseases, degenerative processes, hypoxia, ischemia, metabolic derangements and cancer/radiation (also, intervertebral disk disease for non-TSI). The present invention relates also to individual biomarkers in diagnosing ABI such as mTBI and non-TBI, and ASI, such as mTSI and non-TSI in a subject.

The applicants discovered that metabolomic profiling identifies forms of ACNSI with a relatively high degree of certainty. As of the date of this invention, the predictive ability of the methods of the present invention may be the best biological test to date for mTBI diagnosis. The methods and computer programs of the present invention may be used in point-of-care metabolomics testing with portable, table/counter top or hand held instruments that generate metabolite profiles.

Metabolomic Profiling

Since metabolites exist in a very broad range of concentrations and exhibit chemical diversity, there is no one instrument that can reliably measure all of the metabolites in the non-human or human metabolome in a single analysis. Instead, practitioners of metabolomic profiling generally use a suite of instruments, most often involving different combinations of liquid chromatography (LC) or gas chromatography (GC) coupled with MS, to obtain broad metabolic coverage [Circulation. 2012; 126: 1110-1120] Although in this invention NMR and Direct Injection LC-MS/MS (DI/LC-MS/MS) metabolic profiling were used, it should be understood that other instruments such as electrochemical analysis, RI, UV, near-IR, LS, GC and so forth may also be used.

Figure 4:
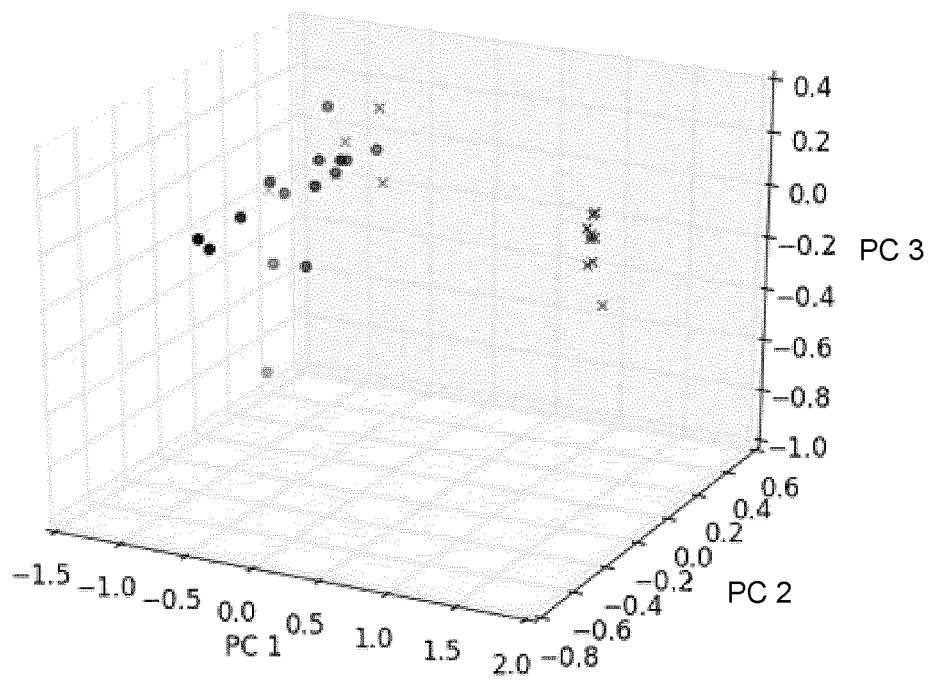
FIG. 4: Graph of individual animals plotted in a 3-dimensional scatter plot of the leading 3 components (15 blast animals—filled circle, 15 control animals—'X').

NMR and DI-LC-MS/MS metabolic profiles obtained from individuals known to have a mTBI and non-mTBI individuals ("controls" or "normals") were analyzed individually employing unsupervised dimensionality-reduction techniques; a mTBI predicting classifier was constructed using supervised machine-learning methods. Specifically: the raw DI-LC-MS/MS and/or NMR data obtained from biological specimens were normalized and subjected to either or both Principle Component Analysis (PCA) and t-distributed stochastic nearest neighbor embedding (t-SNE). In all cases for PCA, the leading 10 eigenvectors explained more than 80% of the variance so the trailing eigenvectors were dropped. The metabolite loadings in the top 10 eigenvectors were recorded and each subject was projected into PCA space to inspect subject-component loadings. Two and three dimensional scatter plots of the leading 2 (resp. 3) components revealed strong clustering of mTBI vs. control subjects (FIGS. 1 and 4). Based on the strength of this result, a linear kernel Support Vector Machine (SVM) was trained to classify mTBI subjects from an input metabolic profile. A 10-fold cross validation of the classifier was performed which yielded greater than about 80% accuracy on DI-LC-MS/MS raw data alone, and between about 90-92% on just DI-LC-MS/MS data alone with reduced number of metabolites, greater than about 65% accuracy on NMR data alone and about 92% accuracy on combined DI-LC-MS/MS and NMR data. Finally a Pearson product moment coefficient between the metabolic profiles of each pair of patients was completed to yield a correlation matrix. Clear structure was visible in the correlation matrix so complete-linkage hierarchical clustering was performed on the matrix which effectively clustered individuals into a 'mTBI' group, a 'non-mTBI' group and a small heterogeneous group.

Based on the blood plasma metabolomics profiling (DI-LC-MS/MS and NMR together, or DI-LC-M/MS alone), of human patients, mTBI was predicted with approximately 92% certainty.

Point-of-care testing (e.g. table top MS) could be developed to identify ABI, including mTBI and non-TBI patients, and to prognosticate their brain injuries.

As such, in one embodiment, the present invention provides for a method of diagnosing or prognosticating a ACNSI in a subject, including acquired brain injury (ABI) and acquired spinal cord injuries (ASI). The method may include the following steps: (a) obtaining a metabolite profile from the subject; and (b) using multivariate statistical analysis and machine learning to compare the subject's profile with a predetermined set of metabolite profiles of ACNSI injuries and a predetermined set of metabolite profiles of non-ACNSI (referred to as "control" or "normal") to determine or diagnose if the patient has ACNSI injury or prognosticate the ASNSI.

A library of metabolic profiles may be established for diagnosed ABI cases, including mTBIs and non-TBIs. For example, a library of metabolic profiles of concussion, primary blast in blast-induced traumatic brain injury, electrical-induced brain injury (electrocution), seizure-induced brain injury, surgical-induced brain injury, stroke-induced brain injury, poison-induced brain injury, psychological brain injury, chemical brain injury, infectious brain injury, ischemic brain injury, metabolic brain injury, inflammatory brain injury, autoimmune brain injury, degenerative brain injury, hypoxic brain injury, and cancer/radiation-induced brain injury and any other possible form of ABI. This library may be used as the predetermined set of metabolic profiles of ABI. Similarly, libraries may be established for diagnosed ASI cases to obtain predetermined set of metabolic profiles of ASI. The predetermined set of normal metabolic profiles may be obtained from subjects known not to have a form of ABI and/or ASI. Using multivariate statistical analysis and machine learning a comparison may be made of the subject's profile with the predetermined set of metabolite profiles of ABI/ASI and the predetermined set of metabolite profiles of non-ABI/non-ASI (referred to as "control" or "normal") to determine not only if the patient has ABI/ASI, but also the type of ABI/ASI (i.e. concussion, primary blast in blast-induced traumatic brain injury, electrical-induced brain injury (electrocution), seizure-induced injury, surgical-induced injury, stroke-induced injury, poison-induced injury, psychological injury, chemical injury, infectious injury, ischemic injury, metabolic injury, inflammatory injury, autoimmune injury, degenerative injury, hypoxic injury, and cancer/radiation-induced injury and so forth) and the prognosis.

The libraries of predetermined profiles (ABI, ASI and controls) may be provided in a computer product (memory sticks, as an app for hand-held devices such as pads and cellular phones and so forth), or they may be uploaded to the memory of a computer system, including main frames, desktops, laptops, hand-held devices such as pads and cellular phones. Blood or any other bodily fluid, for example whole blood, blood plasma, blood serum, saliva, synovial fluid, urine, spinal fluid, bronchoalveolar lavage, tears, sweat, extracts and so forth, may be taken from a subject suspected of having an ABI and/or ASI. A metabolite profile may be obtained from the subject's fluid using any known technology (for example, high performance liquid chromatography, thin layer chromatography, electrochemical analysis, mass spectroscopy (MS), refractive index spectroscopy, ultra-violet spectroscopy, fluorescent analysis, radiochemical analysis, near-infrared spectroscopy, nuclear magnetic resonance (NMR), light scattering analysis, gas chromatography (GC), or GC coupled with MS, direct injection (DI) coupled with LC-MS/MS and so forth). The subject's metabolite profile may then be uploaded to the computer system (main frames, desktops, laptops, hand-held devices and so forth). An operator may then compare the subject's profile with the predetermined set of metabolite profiles of ABI and/or ASI and the predetermined set of metabolite profiles of non-ABI/non-ASI (referred to as "control" or "normal") using multivariate statistical analysis and machine learning to determine not only if the patient has ABI and/or ASI, but also the type of ABI and/or ASI, or whether a treatment is efficient. The operator may select the type of multivariate analysis and machine learning.

Returns to a normal metabolomic profile may serve as an aid in following medical interventions (including rehabilitation therapy) of individuals affected by an ABI, ASI, mTSI, non-TSI, mTBI and/or non-TBI, and guide return to pre-ABI/pre-ASI play, school, work and/or daily activities.

As such, in another embodiment, the present invention is a method of tracking or following the efficiency of a medical intervention (including rehabilitation therapy) in an ACNSI patient, including mTSI patient, non-TSI patient, mTBI patient and non-TBI patient, the method including: (a) obtaining metabolite profiles from the patient at different times during the medical intervention (including rehabilitation therapy); and (b) using multivariate statistical analysis and machine learning to compare the patient's profiles during or at each of the different times with a predetermined set of metabolite profiles of ACNSI and a predetermined set of metabolite profiles of non-ACNSI (normal control) to follow the efficiency of the medical intervention in the patient. A return to a normal metabolomic profile of the patient may serve to assess whether the medical intervention (including rehabilitation therapy) of the patient has been successful.

In one embodiment, the present invention is a method of assessing a non-human animal model of human ACNSI, including mTBI and non-TBI as well as mTSI and non-TSI. The method may be used for determining animal models that best represent the human condition, which may be useful for therapeutic intervention and discovery. The method, in one embodiment, may include: (a) obtaining a metabolite profile from the non-human animal model of ACNSI; and (b) using multivariate statistical analysis and machine learning to compare the non-human animal model profile with a predetermined set of metabolite profiles of human ACNSI and a predetermined set of metabolite profiles of human non-ACNSI to determine if the non-human animal has ACNSI. The non-human animal model may be considered an accurate, reliable and reproducible model of human ACNSI if it is classified as ACNSI. The non-human animal model may be a model of human ACNSI if it is classified as ACNSI with a predetermined level of accuracy or certainty.

In order to aid in the understanding and preparation of the within invention, the following illustrative, non-limiting, examples are provided.

EXAMPLES

Example 1

Materials and Methods

The human research ethics board at Western University approved this study. Informed consent was obtained from the legal guardians and assent was obtained from adolescent subjects.

Subject Recruitment:

Male adolescent ice hockey athletes (Bantam Division; aged 12-14 years) from South Western Ontario, Canada were recruited to participate in this study. To aid recruitment, a study information poster was displayed in City Ice Hockey Arenas, with consent of Arena officials, and verbal presentations made to several regional hockey boards and coaches. Adolescent hockey athletes that presented to Primary Care Physicians at the Fowler Kennedy Sports Medicine Clinic at Western University with a suspected concussion were screened and approached for consent. A diagnosis of sport concussion was made when there was an observed mechanism of injury followed by onset of typical concussive symptoms, and the absence of structural injury. Control subjects were non-injured hockey players that were age-, sex- and activity-matched, and that had not suffered a past concussion. Any subject with a known neurological insult or disease was excluded. After recruitment, all study subjects were assigned a random study number for identification. No further subject identifiers were used in order to protect identity.

Concussed and control subjects, including their parents/guardians, completed a Sport Concussion Assessment Tool-3rd edition [SCAT3; 13-14 years of age; (Guskiewicz et al., 2013)] or a Child-SCAT3[(a modified tool recommended for children 12 year of age or young that takes into account developmental differences in performance (Glaviano et al., 2015)]. All injured athletes underwent a complete history, physical and neurologic examination by a sports medicine physician with expertise in concussion management. The injured athletes were provided with standardized care for concussion led by a Primary Care Sports Medicine physician.

All subjects on the first clinic visit had 20 ml of blood drawn by a certified phlebotomist, nurse or physician into EDTA Vacutainer tubes. The blood was centrifuged, and the plasma aliquoted and stored at −80° C.

DI-LC/MS/MS

A targeted quantitative metabolomics approach was applied to analyze the plasma samples using a combination of direct injection mass spectrometry (AbsoluteIDQ™ Kit) with a reverse-phase LC/MS/MS Kit (BIOCRATES Life Sciences AG, Austria). This kit, in combination with an ABI 4000 Q-Trap (Applied Biosystems/MDS Sciex) mass spectrometer, can be used for the targeted identification and quantification of up to 180 different endogenous metabolites including amino acids, acylcarnitines, biogenic amines, glycerophospholipids, sphingolipids and sugars. The method combines the derivatization and extraction of analytes, and the selective mass-spectrometric detection using multiple reaction monitoring pairs. Isotope-labeled internal standards and other internal standards are integrated in the Kit plate filter for metabolite quantification. The AbsoluteIDQ kit contained a 96 deep-well plate with a filter plate attached with sealing tape, and reagents and solvents used to prepare the plate assay. The first 14 wells in the Kit were used for one blank; three zero samples, seven standards and three quality control samples provided with each Kit. All the plasma samples were analyzed with the AbsoluteIDQ kit protocol, as per the user manual. Briefly, plasma samples were thawed on ice and then vortexed and centrifuged at 13,000×g. Each plasma sample (10 µL) was loaded onto the center of the filter on the upper 96-well kit plate and dried in a stream of nitrogen. Subsequently, 20 µL of a 5% solution of phenyl-isothiocyanate was added for derivatization. After incubation, the filter spots were dried again using an evaporator. Extraction of the metabolites was then achieved by adding 300 µL methanol containing 5 mM ammonium acetate. The extracts were obtained by centrifugation into the lower 96-deep well plate, followed by a dilution step with kit MS running solvent. Mass spectrometric analysis was performed on an API4000 Qtrap® tandem mass spectrometry instrument (Applied Biosystems/MDS Analytical Technologies, Foster City, Calif.) equipped with a solvent delivery system. The samples were delivered to the mass spectrometer by LC followed by a DI. The Biocrates MetIQ software was used to control the entire assay workflow, from sample registration to automated calculation of metabolite concentrations. A targeted profiling scheme was used to quantitatively screen for known small molecule metabolites using multiple reaction monitoring, neutral loss and precursor ion scans.

NMR

Plasma samples were deproteinized by ultra-filtration as previously described (Psychogios et al., 2011). Prior to filtration, 3 KDa cut-off centrifugal filter units (Amicon Microcon YM-3) were rinsed five times each with 0.5 mL of $H_2O$ and centrifuged (10,000 rpm for 10 minutes) to remove residual glycerol bound to the filter membranes. Aliquots of each plasma sample were then transferred into the centrifuge filter devices and centrifuged (10,000 rpm for 20 minutes) to remove macromolecules (primarily protein and lipoproteins) from the sample. The filtrates were checked visually for any evidence that the membrane was compromised and for these samples the filtration process was repeated with a different filter and the filtrate inspected again. The subsequent filtrates were collected and the volumes were recorded. If the total volume of the sample was under 600 µL an appropriate amount from a 50 mM $NaH_2PO_4$ buffer (pH 7.0) was added until the total volume of the sample was 600 µL. Any sample that had to have buffer added to bring the solution volume to 600 µL, was annotated with the dilution factor and metabolite concentrations were corrected in the subsequent analysis. Subsequently, 70 µL of $D_2O$ and 30 µL of a standard buffer solution (11.7 mM DSS (disodium-2,2-dimethyl-2-silcepentane-5-sulphonate], 730 mM imidazole, and 0.47% $NaN_3$ in $H_2O$) was added to the sample.

The plasma sample (700 µL) was then transferred to a standard NMR tube for subsequent spectral analysis. All $^1$H-NMR spectra were collected on a 500 MHz Inova (Varian Inc. Palo Alto, Calif.) spectrometer equipped with a 5 mm HCN Z-gradient pulsed-field gradient room-temperature probe. 1H-NMR spectra were acquired at 25° C. using the first transient of the NOESY—pre-saturation pulse sequence, chosen for its high degree of quantitative accuracy (Saude et al., 2006). All FID's (free induction decays) were zero-filled to 64 K data points and subjected to line broadening of 0.5 Hz. The singlet produced by the DSS methyl groups was used as an internal standard for chemical shift referencing (set to 0 ppm) and for quantification all $^1$H-NMR spectra were processed and analyzed using the Chenomx NMR Suite Professional Software package version 7.1 (Chenomx Inc, Edmonton, AB). The Chenomx NMR Suite software allows for qualitative and quantitative analysis of an NMR spectrum by manually fitting spectral signatures from an internal database to the spectrum. Specifically, the spectral fitting for metabolite was done using the standard Chenomx 500 MHz metabolite library. Typically 90% of visible peaks were assigned to a compound and more than 90% of the spectral area could be routinely fit using the Chenomx spectral analysis software. Most of the visible peaks are annotated with a compound name. It has been previously shown that this fitting procedure provides absolute concentration accuracy of 90% or better. Each spectrum was processed and analyzed by at least two NMR spectroscopists to minimize compound misidentification and mis-quantification. We used sample spiking to confirm the identities of assigned compounds. Sample spiking involves the addition of 20-200 µM of the suspected compound and examination of the resulting spectra to determine whether the relative NMR signal intensity changed as expected.

Data Analyses

Demographic and concussion tool data were reported as mean±standard deviation (SD), with a P value <0.05 taken as our standard of statistical significance. Raw NMR and MS data for each subject were ingested and normalized within each metabolite marker, across subjects. More specifically, the data for each metabolic marker were scaled to have unit norm. Initial exploratory analysis involved performing Principal Component Analysis (PCA) directly on the subjects by metabolites matrix. Motivated by the observation that the inherent dimensionality of the data was significantly lower that the number of metabolite markers, Nonlinear dimensionality reduction was performed on the full data matrix using the t-distributed stochastic nearest neighbour (t-SNE) embedding algorithm (van der Maaten and Hinton, 2008). Unlike PCA which enforces a brittle, orthogonal, linear refactorization of the data, t-SNE assumes that the 'optimal' representation of the data lies on a manifold with complex geometry, but low dimension, embedded in the full dimensional space of the raw data. t-SNE was used to reduce the full metabolic dataset down to only two dimensions. We then trained separate support vector machines (SVM), with linear kernels, on the dimensionality reduced and full datasets to classify subjects as concussed or non-concussed. We cross-validated our classifier using a leave-one-out approach and assessed statistical significance against a null distribution generated by resampling. To investigate the robustness of the trained classifier, a Receiver Operating Characteristic (ROC) curves were generated; one curve was generated for each fold of a 4-fold cross-validation approach where the classifier for each fold is trained on a subset of the data and then tested on a disjoint, withheld, subset that was not used for training. The ROC curve plots the true positive rate against the false positive rate of the classifier; the top left corner of the plot is "ideal" and the main diagonal would be occupied by a classifier that simply guessed randomly at labels.

Results

Metabolomics

Plasma was assayed from male adolescent ice hockey players: 12 concussed (13.4±2.3 years of age) and 17 non-injured controls (12.9±1.0 years of age; P=0.213). The estimated time from concussion occurrence to blood draw at the first clinic visit was 2.3±0.7 days.

Self-reported symptom evaluation as per SCAT3 (n=11) revealed a total symptom score and a total symptom severity of 11.6±4.8 and 29.3±22.8, respectively (Table 1). One concussed patient was evaluated with the Child SCAT and had a total symptom score of 6 and a total symptom severity of 12. All non-injured controls were evaluated with a SCAT3 (n=17), which revealed a total symptom score and a total symptom severity of 0.5±1.5 and 0.6±1.8, respectively.

Plasma was assayed for 143 and 31 metabolites by DI/LC-MS/MS (Table 2) and NMR (Table 3), respectively.

PCA

Using PCA, the leading 10 components were demonstrated to account for 82% of the variance in the data, with each of the 10 components weighted across many of the underlying metabolites (Table 4). The most striking observation was the high variance in plasma glycerophospholipids between concussed and non-concussed subjects.

t-SNE

The full metabolic dataset was reduced down to two dimensions using t-SNE, as the inherent dimensionality of the data was significantly lower than the number of metabolites (FIG. 1). Following this dimensionality reduction step, a support vector machine (SVM) was trained, with a linear kernel, to classify subjects as concussed or non-concussed. Cross validation of the classifier using a leave-one-out approach demonstrated a 92% accuracy rate in diagnosing a concussion in adolescent ice hockey players.

Taking classification accuracy as our test statistic, we investigate the significance of our observed accuracy via permutation testing. We generated a null distribution by randomly shuffling class labels; training and testing a new classifier for each shuffled label set and recording the classification rate. Comparing our observed 92% accuracy rate to a 10,000 sample null distribution in which none of the null classifiers reached a 92% accuracy rate, we calculated a $p<0.0001$.

We then minimized the number of metabolites required to achieve reasonable classification accuracy. Using a chi-square test to select informative metabolites in a univariate manner, we continued to observe 92% classification accuracy with only 17 metabolites (Table 5, Column 1). Recursive feature elimination was then used to verify accuracy, and yielded a similar classification accuracy of 90% with 31 metabolites (Table 5, Column 2).

Figure 2:
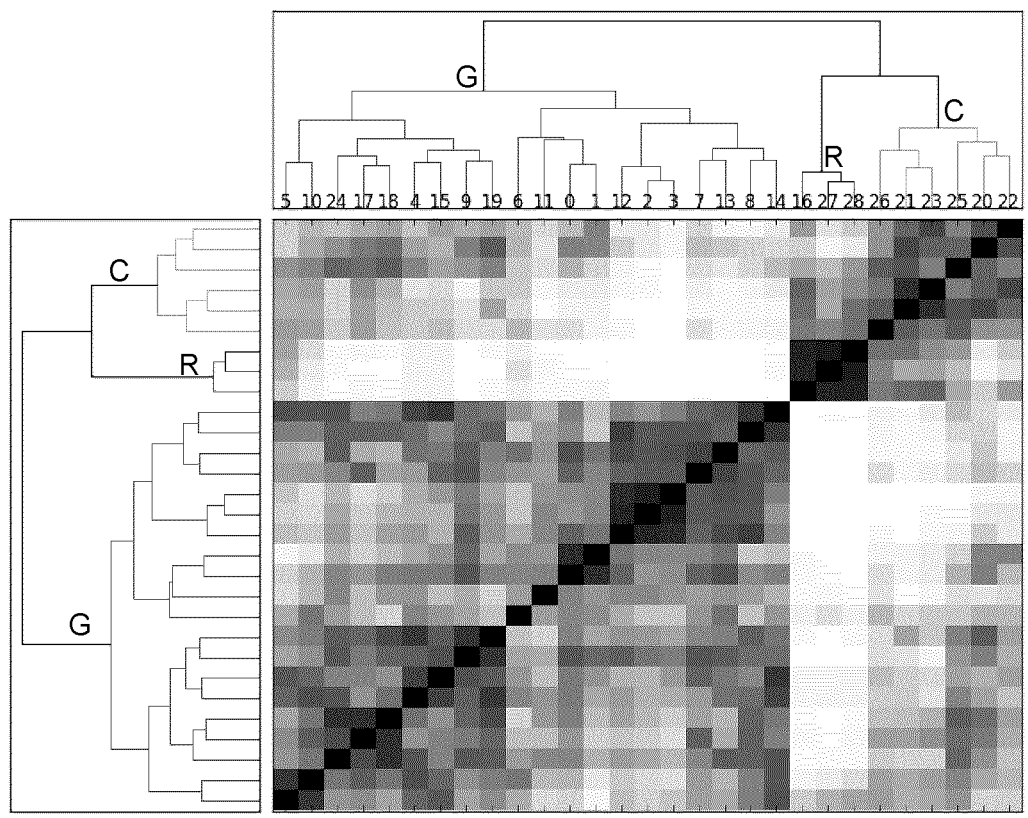
FIG. 2: Graph illustrating agglomerative complete-linkage hierarchical clustering, yielding 3 top level clusters: Green ("G") cluster—all concussed, but 2, Cyan ("C") cluster—all concussed, Red ("R") cluster—two concussed, one control).

As a final step, we clustered concussed and non-concussed subjects by direct comparison of their metabolomic profiles. We computed the Pearson product-moment coefficient for each pair of (normalized) subject metabolic profiles to yield a correlation matrix. Clusters were optimally identified in this correlation matrix with agglomerative complete-linkage hierarchical clustering (FIG. 2).

Figure 3:
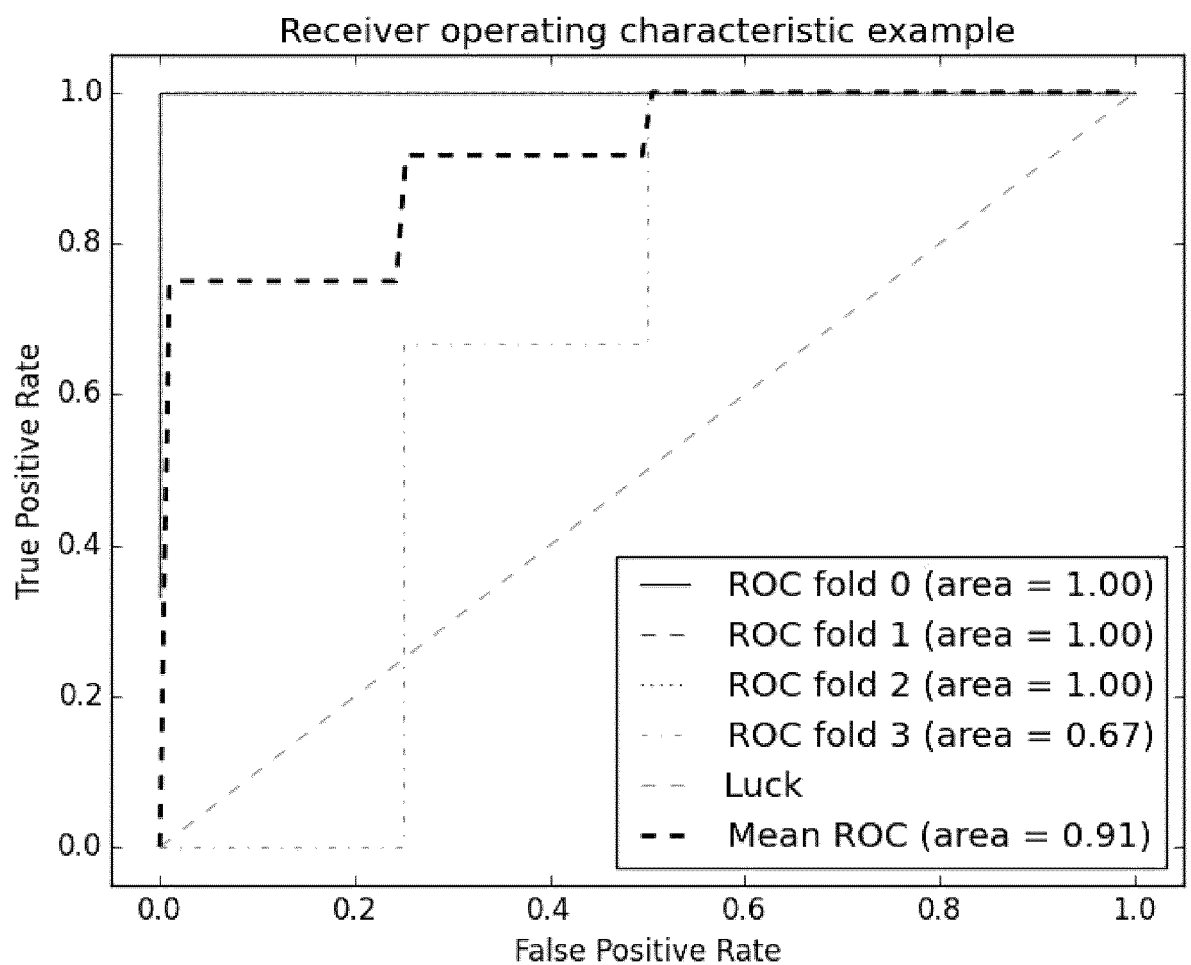
FIG. 3: Graph illustrating a Receiver Operating Curve (ROC). Note that the curves for ROC fold 0, ROC fold 1 and ROC fold 2 are superimposed.

A receiver operating curve was generated over a 4-fold cross-validation with a SVM (FIG. 3), demonstrating the performance of a binary classifier as its discrimination threshold is varied, and yielding a mean ROC of 0.91.

TABLE 1

Symptom Evaluation via SCAT3 (1 patient not shown as had a child SCAT)*

| Symptom | # of Symptoms (n = 11) | Percent (%) |
|---|---|---|
| Headache | 10 | 91% |
| Dizziness | 9 | 82% |
| Pressure in head | 9 | 82% |
| Sensitivity to light | 9 | 82% |
| Don't feel right | 9 | 82% |
| Difficulty concentrating | 8 | 73% |
| Fatigue or low energy | 8 | 73% |
| Sensitivity to noise | 8 | 73% |
| Feeling slowed down | 8 | 73% |
| Drowsiness | 7 | 64% |
| Balance problems | 7 | 64% |
| Trouble falling asleep | 7 | 64% |
| Difficulty remembering | 6 | 55% |
| Neck Pain | 5 | 45% |
| Blurred vision | 4 | 36% |
| Feeling like in a fog | 4 | 36% |
| Confusion | 4 | 36% |
| Irritability | 3 | 27% |
| Nausea or vomiting | 2 | 18% |
| More emotional | 1 | 9% |
| Sadness | 1 | 9% |
| Nervous or Anxious | 1 | 9% |

*1 patient is not shown as they had symptom evaluation via a Child SCAT3 (reported symptoms: difficulty paying attention; I daydream too much; headache; dizzy; tired a lot; and tired easily).

TABLE 2

DI-LC/MS/MS (143 metabolites)

| | | | | |
|---|---|---|---|---|
| C0 | PC aa C32:1 | PC ae C30:0 | PC ae C42:4 | Isoleucine |
| C14:1 | PC aa C32:2 | PC ae C30:1 | PC ae C42:5 | Leucine |

TABLE 2-continued

DI-LC/MS/MS (143 metabolites)

| | | | | |
|---|---|---|---|---|
| C14:2 | PC aa C32:3 | PC ae C32:1 | PC ae C44:3 | Lysine |
| C16 | PC aa C34:1 | PC ae C32:2 | PC ae C44:4 | Methionine |
| C18 | PC aa C34:2 | PC ae C34:0 | PC ae C44:5 | Ornithine |
| C18:1 | PC aa C34:3 | PC ae C34:1 | PC ae C44:6 | Phenylalanine |
| C18:2 | PC aa C34:4 | PC ae C34:2 | SM (OH) C14:1 | Proline |
| C2 | PC aa C36:0 | PC ae C34:3 | SM (OH) C16:1 | Serine |
| C3 | PC aa C36:1 | PC ae C36:0 | SM (OH) C22:1 | Threonine |
| C4 | PC aa C36:2 | PC ae C36:1 | SM (OH) C22:2 | Tryptophan |
| C5 | PC aa C36:3 | PC ae C36:2 | SM (OH) C24:1 | Tyrosine |
| C5-OH (C3-DC-M) | PC aa C36:4 | PC ae C36:3 | SM C16:0 | Valine |
| C9 | PC aa C36:5 | PC ae C36:4 | SM C16:1 | Acetyl-Ornithine |
| lysoPC a C16:0 | PC aa C36:6 | PC ae C36:5 | SM C18:0 | Asymmetricdimethylarginine |
| lysoPC a C16:1 | PC aa C38:0 | PC ae C38:0 | SM C18:1 | Total Dimethylarginin |
| lysoPC a C17:0 | PC aa C38:1 | PC ae C38:1 | SM C20:2 | alpha-Aminoadipic |
| lysoPC a C18:0 | PC aa C38:3 | PC ae C38:2 | SM C22:3 | Creatinine |
| lysoPC a C18:1 | PC aa C38:4 | PC ae C38:3 | SM C24:0 | Kynurenine |
| lysoPC a C18:2 | PC aa C38:5 | PC ae C38:4 | SM C24:1 | Methionine-Sulfoxide |
| lysoPC a C20:3 | PC aa C38:6 | PC ae C38:5 | SM C26:0 | trans-OH-Proline |
| lysoPC a C20:4 | PC aa C40:2 | PC ae C38:6 | SM C26:1 | Putrescine |
| lysoPC a C26:0 | PC aa C40:3 | PC ae C40:1 | H1 | Spermine |
| lysoPC a C26:1 | PC aa C40:4 | PC ae C40:2 | Alanine | Taurine |
| lysoPC a C28:0 | PC aa C40:5 | PC ae C40:3 | Arginine | |
| lysoPC a C28:1 | PC aa C40:6 | PC ae C40:4 | Asparagine | |
| PC aa C24:0 | PC aa C42:0 | PC ae C40:5 | Citrulline | |
| PC aa C28:1 | PC aa C42:1 | PC ae C40:6 | Gltamine | |
| PC aa C30:0 | PC aa C42:4 | PC ae C42:1 | Glutamic acid | |
| PC aa C30:2 | PC aa C42:5 | PC ae C42:2 | Glycine | |
| PC aa C32:0 | PC aa C42:6 | PC ae C42:3 | Histidine | |

TABLE 3

NMR (31 metabolites)

2-Hydroxybutyrate
3-Hydroxybutyrate
3-Hydroxyisovalerate
Acetate
Acetone
Alanine
Betaine
Carnitine
Citrate
Creatine
Creatinine
Formate
Glucose
Glutamine
Glycerol
Glycine
Histidine
Isoleucine
Lactate
Leucine
Lysine
Methanol
Phenylalanine
Proline
Propylene glycol
Pyruvate
Serine
Succinate
Threonine
Tyrosine
Valine

TABLE 4

PCA identified the top 10 weighted metabolites for each of the 10 leading components ("Comp.").

| Comp. 0 (Explained variance: 28.21%) | Comp. 1 (Explained variance: 14.83%) | Comp. 2 (Explained variance: 9.7%) | Comp. 3 (Explained variance: 6.1%) | Comp. 4 (Explained variance: 5.76%) |
|---|---|---|---|---|
| PC aa C36:0 (0.171) | C5-OH (C3-DC-M) (0.073) | PC aa C36:0 (0.233) | C14:2 (0.183) | Isoleucine (0.158) |
| PC aa C36:5 (0.185) | lysoPC a C18:2 (0.044) | PC aa C36:5 (0.253) | C2 (0.181) | Leucine (0.155) |
| PC aa C36:6 (0.16) | PC aa C36:0 (0.041) | PC aa C38:0 (0.265) | SM C22:3 (0.243) | alpha-Aminoadipic acid (0.147) |
| PC aa C38:0 (0.151) | PC aa C36:5 (0.055) | PC aa C38:1 (0.221) | Arginine (0.177) | Putrescine (0.402) |
| PC aa C38:6 | PC aa C36:6 | PC aa C38:6 | Citrulline (0.13) | -3-Hydroxybutyrate (0.202) |
| | | | Putrescine (0.238) | Creatine (0.115) |
| | | | Acetone (0.402) | |
| | | | Carnitine (0.242) | |
| | | | Glycerol (0.186) | Isoleucine (0.15) |

TABLE 4-continued

PCA identified the top 10 weighted metabolites for each of the 10 leading components ("Comp.").

| | | | | |
|---|---|---|---|---|
| (0.165) | (0.039) | (0.249) | | Leucine (0.134) |
| PC aa C40:6 | PC aa C38:1 | PC aa C40:6 | | Proline (0.106) |
| (0.17) | (0.046) | (0.275) | | |
| PC ae C38:0 | PC ae C38:1 | PC aa C42:0 | | |
| (0.143) | (0.039) | (0.155) | | |
| PC ae C38:1 | PC ae C38:2 | PC ae C38:6 | | |
| (0.146) | (0.04) | (0.152) | | |
| PC ae C40:6 | Citrulline | PC ae C40:6 | | |
| (0.142) | (0.114) | (0.175) | | |

| Comp. 5 (Explained varience: 5.61%) | Comp. 6 (Explained varience: 3.84%) | Com. 7 Explained varience: 2.97%) | Comp. 8 Explained varience: 2.63%) | Comp. 9 (Explained varience: 2.46%) |
|---|---|---|---|---|
| C14:2 (0.152) | lysoPC a C26:0 (0.137) | C3 (0.102) | PC aa C40:3 (0.099) | PC ae C36:2 (0.117) |
| C18:1 (0.173) | lysoPC a C26:1 (0.119) | C5 (0.157) | PC ae C38:1 (0.116) | PC ae C36:5 (0.108) |
| C18:2 (0.156) | lysoPC a C28:1 (0.109) | PC aa C30:2 (0.184) | PC ae C42:4 (0.11) | SM (OH) C14:1 (0.136) |
| C3 (0.169) | PC ae C30:1 (0.251) | PC aa C32:2 (0.116) | Asymmetricdimethylarginine (0.116) | SM C26:0 (0.126) |
| C5 (0.212) | PC ae C38:1 (0.137) | Proline (0.109) | Putrescine (0.372) | trans-OH-Proline (0.418) |
| trans-OH-Proline (0.228) | Putrescine (0.165) | trans-OH-Proline (0.141) | 3-Hydroxyisovalerate (0.565) | 3-Hydroxyisovalerate (0.162) |
| Putrescine (0.244) | Acetone (0.336) | Acetone (0.161) | Acetone (0.156) | Methanol (0.179) |
| 3-Hydroxybutyrate (0.259) | Carnitine (0.179) | Carnitine (0.267) | Carnitine (0.128) | Propylene glycol (0.109) |
| 3-Hydroxyisovalerate (0.264) | Succinate (0.134) | Proline (0.108) | Propylene glycol (0.248) | Succinate (0.324) |

TABLE 5

Similar classification accuracy, using two independent analytical techniques, achieved with fewer metabolites.

| 92% accuracy determined with a Chi Square test | 90% accuracy determined with Recursive Feature Elimination |
|---|---|
| 1. 'C5' | 1. 'C5' |
| 2. 'PC aa C32:1' | 2. 'PC aa C30:2' |
| 3. 'PC aa C32:2' | 3. 'PC aa C32:0' |
| 4. 'PC aa C36:5' | 4. 'PC aa C32:1' |
| 5. 'PC aa C36:6' | 5. 'PC aa C32:2' |
| 6. 'PC ae C34:0' | 6. 'PC aa C32:3' |
| 7. 'PC ae C34:3' | 7. 'PC aa C34:4' |
| 8. 'PC ae C36:0' | 8. 'PC aa C36:6' |
| 9. 'PC ae C36:1' | 9. 'PC aa C42:6' |
| 10. 'PC ae C36:2' | 10. 'PC ae C30:0' |
| 11. 'PC ae C38:1' | 11. 'PC ae C30:1' |
| 12. 'PC ae C38:2' | 12. 'PC ae C32:1' |
| 13. 'PC ae C38:3' | 13. 'PC ae C34:0' |
| 14. 'Putrescine' | 14. 'PC ae C34:2' |
| 15. 'Formate' | 15. 'PC ae C34:3' |
| 16. 'Methanol' | 16. 'PC ae C36:0' |
| 17. 'Succinate' | 17. 'PC ae C36:2' |
| | 18. 'PC ae C38:1' |
| | 19. 'PC ae C38:3' |
| | 20. 'SM C22:3' |
| | 21. 'SM C24:0' |
| | 22. 'SM C24:1' |
| | 23. 'alpha-Aminoadipic acid' |
| | 24. 'trans-OH-Proline' |
| | 25. 'Putrescine' |
| | 26. 'Betaine' |
| | 27. 'Formate' |
| | 28. 'Glucose' |
| | 29. 'Glycerol' |
| | 30. 'Methanol' |
| | 31. 'Serine' |

In this study, we performed metabolomics profiling on concussed adolescent ice hockey players and matched controls. Using multivariate statistical analysis and machine learning, we predicted concussed individuals with up to 92% certainty. One of the most striking patterns observed was the reliance of the model on changes in plasma glycerophospholipids, accounting for approximately 50% of the variance between concussed and non-concussed subjects. Metabolomics profiling with machine learning is a novel concussion diagnostic method with high sensitivity.

We specifically investigated concussion in adolescent ice hockey players. In our region, adolescent males are at the highest risk for concussion, and most frequently concussed in sport-related activities at ice hockey arenas (Stewart et al., 2014). Concussions in these adolescent patients are of particular concern as their brains are still developing (Halstead et al., 2010; Toledo et al., 2012). Younger patients are also more susceptible to injury due to thinner skulls, weaker neck muscles, less myelination, greater brain water content, higher metabolic requirements and a larger subarachnoid space in which the brain can move more freely (Karlin, 2011; Morrison et al., 2013). Subsequently, the rates of concussion are higher in the young and the time to recovery is prolonged relative to adults (Lovell et al., 2004; Pellman et al., 2006). In fact, brain injury may have life-long consequences for adolescents via interrupted intellectual and social development (Toledo et al., 2012). Accurate concussion diagnosis is particularly important for adolescents, as rapid deployment of appropriate early treatment and rehabilitation services could be life-changing for this vulnerable population.

At present, concussion diagnosis is based solely on clinical judgment. Concussion patients in our study were diagnosed by a mechanism of injury with typical concussion symptoms. Patients were assessed with either the SCAT3, or the Child-SCAT3 for one 12 year old subject, as these are the recommended concussion assessment tools for these age groups (Guskiewicz et al., 2013; Glaviano et al., 2015). Based on the average number of self-reported symptoms and the symptom severity score, our data suggests mild-moderate symptom severity of our concussed male athletes. Moreover, to the best of our knowledge, ours is the first study to report normative SCAT3 values for non-injured adolescent male athletes. Self-reporting of symptoms is complicated by the subjective nature of the assessment, and athletes typically underreport the symptoms (Lovell and Solomon, 2013; Meier et al., 2015).

Concussion diagnostics remains problematic, with clinical judgment as the gold standard (McCrory et al., 2013). Thus, there has been an active search for a diagnostic blood biomarker (eg. GFAP, Tau, NFL). Despite a large body of research, no single biomarker or biomarker panel has been identified for widespread diagnostics, likely due to inadequate sensitivity, specificity or reproducibility (Deter et al., 2013). A single biomarker or a small number of biomarkers may not accurately reflect the patient and injury heterogeneity that occurs in brain trauma. Additional concerns relate to individual biomarkers being compared to variable definitions of concussion, to inconsistent use of common clinical and biomarker-related data elements, to the variable timing of outcome measures and to lack of understanding of individual temporal profiles (Papa et al., 2015). Our metabolomics profiling, with 174 metabolites examined and as few as 17 metabolites required for classification accuracy, may be useful for developing future point-of-care testing and a decision-support system for future concussion diagnostics (i.e. internet interface).

Conventional statistics are model-driven in that they are based on the assumption that there are a relatively small number of important variables and that careful variable selection is the key to good model performance. This approach has provided important clinical information on populations, but is significantly limited for understanding disease in individuals. A supplement to conventional statistics is machine learning, that lets the data create the model by detecting underlying patterns (Shouval et al., 2014). Metabolomics is ideally suited for machine learning techniques, as the final performance of the model relies on how much information each dataset contains.

Metabolomics profiling requires analyses of all detected metabolites simultaneously, with PCA analysis techniques used most commonly (Bujak et al., 2014). Unlike PCA which enforces a brittle, orthogonal, linear refactorization of the data, t-SNE assumes that the 'optimal' representation of the data lies on a manifold with complex geometry, but low dimension, embedded in the full dimensional space of the raw data (van der Maaten and Hinton, 2008). The power of the t-SNE dimensionality reduction step was seen once individual subjects were plotted in the reduced 2-dimensional space.

Using the aforementioned analytics, we determined that the variance in metabolites between concussed and non-concussed subjects was most pronounced for the glycerophospholipids. Glycerophospholipids are dynamic molecules, which turn over at different rates depending on their structure, composition and localization in cellular membranes. With respect to the brain, glycerophospholipids account for ~25% of dry weight and are heavily concentrated in myelin (Farooqui et al., 2000). Glycerophospholipids regulate membrane fluidity and permeability, and they are a reserve for a variety of second messengers. Degradation of glycerophospholipids occurs via phospholipases.

Once the number of metabolites was reduced, but still maintained high classification accuracy, the most informative were choline glycerophospholipids with a number of choline plasmalogens (e.g., PCaeC34:0, PCaeC34:3, PCaeC36:0, PCaeC36:1, PCaeC36:2, PCaeC38:1, PCaeC38:2 and PCaeC38:3). Plasmalogens are present in significant amounts in myelin, with >70% of myelin glycerophospholipids being plasmalogens (Braverman and Moser, 2012). Plasmalogens are considered to have several functions including contributing to membrane structure, acting as membrane antioxidants and being a source of second messenger molecules.

The acylcarnitine C5 also had a prominent role in classification accuracy. The role of C5 is complex and related to energy metabolism, fatty acid transport and mitochondrial fatty acid oxidation, ketosis, oxidative stress and mitochondrial membrane damage. C5 is produced during the catabolism of the branched chain amino acids leucine and isoleucine. An elevation of C5 acylcarnitine may be an indicator of block at the levels of isovaleryl-CoA dehydrogenase and short/branched chain acyl-CoA dehydrogenase. Other metabolites of importance for accurate classification include putrescine, methanol, formate and succinate. When taken these latter metabolites are taken together, the findings suggest acute changes in brain energy metabolism after concussion in these young athletes (Sikoglu et al., 2015).

Most of the informative metabolites, such as the glycerophospholipids, gather into metabolite groups. Nonetheless, it is difficult to develop a unifying theory. The metabolites identified may reflect secondary consequences to the primary concussive injury or themselves may have common secondary metabolic impacts. Further experimentation using animal models of TBI may be informative where both brain and plasma can be analyzed in parallel.

Normalization of metabolites could reflect tissue healing and recovery, and help guide concussion rehabilitation and safe return to play and other daily activities. Providing an objective measure of recovery through metabolomics has great potential to enhance concussion management by further standardizing return-to-play and return-to-learn practices beyond what legislation and policies can currently provide. This can protect athletes from returning to activities too early which can lead to increased risk of repeat concussions, other injury and the prolongation of symptoms. (Harmon et al, 2013) Finally, clinical judgment is the de facto 'gold standard' for concussion diagnosis and thus concussion may have been over-diagnosed in the "concussed group". Also, previous concussions may have been missed in the "control" group, while sub-clinical brain injuries would not have been accurately represented.

In summary, using plasma metabolomics profiling, together with multivariate statistical analysis and machine learning, we identified concussed individuals with 92% certainty. Of the two analytic techniques used, NMR and DI-LC/MS/MS, the metabolites measured with tandem MS appear to offer greater predictive ability. Indeed, much of the observed variance between groups was due to changes in plasma glycerophospholipids and C5. Metabolomics profiling represents a novel diagnostic method for mTBI, and may be amenable to point-of-care metabolomic testing.

REFERENCES FOR EXAMPLE 1

Braverman N E, Moser A B. Functions of plasmalogen lipids in health and disease. Biochim Biophys Acta 2012; 1822 (9): 1442-52.

Bujak R, Struck-Lewicka W, Markuszewski M J, Kaliszan R. Metabolomics for laboratory diagnostics. Journal of pharmaceutical and biomedical analysis 2014.

Farooqui A A, Horrocks L A, Farooqui T. Glycerophospholipids in brain: their metabolism, incorporation into membranes, functions, and involvement in neurological disorders. Chemistry and physics of lipids 2000; 106(1): 1-29.

Glaviano N R, Benson S, Goodkin H P, Broshek D K, Saliba S. Baseline SCAT2 Assessment of Healthy Youth Student-Athletes: Preliminary Evidence for the Use of the Child-SCAT3 in Children Younger Than 13 Years. Clin J Sport Med 2015; 25(4): 373-9.

Guskiewicz K M, Register-Mihalik J, McCrory P, McCrea M, Johnston K, Makdissi M, et al. Evidence-based approach to revising the SCAT2: introducing the SCAT3. Br J Sports Med 2013; 47(5): 289-93.

Harmon K G, Drezner J A, Gammons M, Guskiewicz K M, Halstead M, Herring S A, Kutcher J S, Pana A, Putakian M, Roberts W O. American Medical Society of Sports Medicine position statement: Concussion in sport. British Journal of Sports Medicine. 2013; 47(1):15-26.

Halstead M E, Walter K D, Council on Sports M, Fitness. American Academy of Pediatrics. Clinical report—sport-related concussion in children and adolescents. Pediatrics 2010; 126(3): 597-615.

Jeter C B, Hergenroeder G W, Hylin M J, Redell J B, Moore A N, Dash P K. Biomarkers for the diagnosis and prognosis of mild traumatic brain injury/concussion. Journal of neurotrauma 2013; 30(8): 657-70.

Karlin A M. Concussion in the pediatric and adolescent population: "different population, different concerns". PM R 2011; 3(10 Suppl 2): S369-79.

Lovell M R, Collins M W, Iverson G L, Johnston K M, Bradley J P. Grade 1 or "ding" concussions in high school athletes. Am J Sports Med 2004; 32(1): 47-54.

Lovell M R, Solomon G S. Neurocognitive test performance and symptom reporting in cheerleaders with concussions. J Pediatr 2013; 163(4): 1192-5 e1.

McCrory P, Meeuwisse W, Aubry M, Cantu B, Dvorak J, Echemendia R J, et al. Consensus statement on concussion in sport—the 4th International Conference on Concussion in Sport held in Zurich, November 2012. Clin J Sport Med 2013; 23(2): 89-117.

Meier T B, Brummel B J, Singh R, Nerio C J, Polanski D W, Bellgowan P S. The underreporting of self-reported symptoms following sports-related concussion. J Sci Med Sport 2015; 18(5): 507-11.

Morrison G, Fraser D D, Cepinskas G. Mechanisms and consequences of acquired brain injury during development. Pathophysiology 2013; 20(1): 49-57.

Papa L, Ramia M M, Edwards D, Johnson B D, Slobounov S M. Systematic review of clinical studies examining biomarkers of brain injury in athletes after sports-related concussion. Journal of neurotrauma 2015; 32(10): 661-73.

Pellman E J, Lovell M R, Viano D C, Casson I R. Concussion in professional football: recovery of NFL and high school athletes assessed by computerized neuropsychological testing—Part 12. Neurosurgery 2006; 58(2): 263-74; discussion—74.

Shouval R, Bondi O, Mishan H, Shimoni A, Unger R, Nagler A. Application of machine learning algorithms for clinical predictive modeling: a data-mining approach in SCT. Bone marrow transplantation 2014; 49(3): 332-7.

Sikoglu E M, Liso Navarro A A, Czerniak S M, McCafferty J, Eisenstock J, Stevenson J H, et al. Effects of Recent Concussion on Brain Bioenergetics: A Phosphorus-31 Magnetic Resonance Spectroscopy Study. Cogn Behav Neurol 2015; 28(4): 181-7.

Stewart T C, Gilliland J, Fraser D D. An epidemiologic profile of pediatric concussions: identifying urban and rural differences. The journal of trauma and acute care surgery 2014; 76(3): 736-42.

Toledo E, Lebel A, Becerra L, Minster A, Linnman C, Maleki N, et al. The young brain and concussion: imaging as a biomarker for diagnosis and prognosis. Neurosci Biobehav Rev 2012; 36(6): 1510-31.

van der Maaten L, Hinton G. Visualizing data using t-SNE. J Mach Learn Res 2008; 9(11): 2579-605.

Example 2—Primary Blast Traumatic Brain Injury

Materials and Methods
Blast Exposure

In conducting this research the authors adhered to the "Guide to the Care and Use of Experimental Animals" and "The Ethics of Animal Experimentation" published by the Canadian Council on Animal Care. Adult male Sprague-Dawley rats were acquired from Charles River Laboratories (St. Constant, Que, Canada) and acclimated for at least one week prior to exposure. There are 15 control and 15 blast samples. On the day of use, the animals (~280-330 g) were anaesthetized with 3% isoflurane in oxygen and placed into a restraint consisting of a clear plastic cylindrical sleeve, with the neck encircled snugly in a plastic collar and the head protruding through an opening in the end, which is concaved such that it matches the curvature of the blast tube interior. The hind quarters were supported using an end cap fitted with a piston. To the left of the head and contralateral to the shock wave direction, a mesh netting was secured between two pins placed vertically in line with the side of, and above and below the head. The motion of the head was restrained using two different methods defined as Head Restraint 1 and 2. With Head Restraint 1, the head was placed against the vertical netting, and then held in place using additional netting around the head. Head Restraint 2 also used the vertical mesh, but with the head of the anaesthetized animal supported using a thin strip of duct tape placed horizontally between the bottom pins. Importantly, this method did not secure the head in place against the vertical mesh with additional netting. After a total of eight min of anaesthesia, the restraint containing the animal was set into the wall of the Advanced Blast Simulator (ABS) 4280 mm downstream from the diaphragm, such that only the head protruded into the test section. Test groups consisted of sham control, while the experimental group consisted of head-only, side-on exposures of single pulse shock wave static overpressures of 30 psi of ~6-7 msec positive duration.

Advanced Blast Simulator (ABS)

A custom-built ABS (~30.5 cm in diameter and 5.79 m in length) was used for producing simulated blast waves. Unlike a conventional shock tube, the ABS was designed from first principles to replicate the wave dynamics of explosive blast by means of its specially shaped divergent area. It is particularly important to reproduce the correct tailored waveforms for static and dynamic pressure in the shockwave which are most often misrepresented in conventional shock tubes. The ABS consists of a "driver" section filled with high-pressure gas separated by a frangible diaphragm from a transition section, leading to an ambient-pressure test section. Controlled pressurization of the driver causes rupture of the diaphragm at predetermined pressures, abruptly releasing the high-pressure gas and driving a tailored shock wave down the length of the test section. The inclusion of an End Wave Eliminator (EWE) at the end of the test section precludes reflected waves propagating back into the testing area; the EWE also mitigates noise and gas efflux into the laboratory space. By means of these unique design features, the ABS generates highly reproducible single-pulse shock waves tailored to replicate those of explosive blast. The required target pressure and waveform shapes were achieved using compressed helium in the driver and various layering and thicknesses of reinforced cellulose acetate sheets for the frangible diaphragm.

ABS Pressure Data Acquisition

Static pressures were measured using PCB 113A28 gauges placed at 2780, 3280, 3780, 4280 and 4780 mm from the diaphragm. Total pressures experienced by the test animal were measured using a Pitot probe (Endevco 8530B pressure transducer) orientated such that it measured the total pressures at the test location 4280 mm from the diaphragm. Dynamic pressures were obtained by calculating the difference between the static and total pressure recorded at this location. All pressure data was recorded using a custom Labview interface and recorded on a GaGe Octopus 8389 CompuScope PCIe digitizer board at a sampling rate of 500,000 samples/sec.

Metabolomics

The rats were humanely sacrificed and the circulating blood volume removed by intracardiac stab. The blood was immediately transferred from the syringe to EDTA containing tubes and centrifuged. The upper plasma layer was removed, aliquoted and stored at −80° C. until assayed.

DI-LC-MS/MS

A targeted quantitative metabolomics approach was applied to analyze the plasma samples using a combination of direct injection mass spectrometry (AbsoluteIDQ™ Kit) with a reverse-phase LC-MS/MS Kit (BIOCRATES Life Sciences AG, Austria). This kit, in combination with an ABI 4000 Q-Trap (Applied Biosystems/MDS Sciex) mass spectrometer, can be used for the targeted identification and quantification of up to 180 different endogenous metabolites including amino acids, acylcarnitines, biogenic amines, glycerophospholipids, sphingolipids and sugars. The method used combines the derivatization and extraction of analytes, and the selective mass-spectrometric detection using multiple reaction monitoring (MRM) pairs. Isotope-labeled internal standards and other internal standards are integrated in Kit plate filter for metabolite quantification. The AbsoluteIDQ kit contained a 96 deep-well plate with a filter plate attached with sealing tape, and reagents and solvents used to prepare the plate assay. First 14 wells in the Kit were used for one blank; three zero samples, seven standards and three quality control samples provided with each Kit. All the plasma samples were analyzed with the AbsoluteIDQ kit protocol, as per the user manual. Briefly, plasma samples were thawed on ice and then vortexed and centrifuged at 13,000×g. Ten µL of each plasma sample was loaded onto the center of the filter on the upper 96-well kit plate and dried in a stream of nitrogen. Subsequently, 20 µL of a 5% solution of phenyl-isothiocyanate was added for derivatization. After incubation, the filter spots were dried again using an evaporator. Extraction of the metabolites was then achieved by adding 300 µL methanol containing 5 mM ammonium acetate. The extracts were obtained by centrifugation into the lower 96-deep well plate, followed by a dilution step with kit MS running solvent. Mass spectrometric analysis was performed on an API4000 Qtrap® tandem mass spectrometry instrument (Applied Biosystems/MDS Analytical Technologies, Foster City, Calif.) equipped with a solvent delivery system. The samples were delivered to the mass spectrometer by LC followed by a DI. The Biocrates MetIQ software was used to control the entire assay workflow, from sample registration to automated calculation of metabolite concentrations to the export of data into other data analysis programs. A targeted profiling scheme was used to quantitatively screen for known small molecule metabolites using multiple reaction monitoring, neutral loss and precursor ion scans.

Data Analyses

Raw DI-LC-MS/MS data for each animal were ingested and normalized within each metabolite marker, across subjects (specifically: the data for each metabolic marker were scaled to have unit norm). Initial exploratory analysis involved performing Principal Component Analysis (PCA) directly on the animals×metabolites matrix.

The full metabolic raw dataset was also reduced down to two dimensions using t-SNE, as the inherent dimensionality of the data was significantly lower that the number of metabolites. Following this dimensionality reduction step, a SVM was trained, with a linear kernel, to classify subjects as concussed or non-concussed.

Results

PCA Analysis

FIG. 4 is a PCA plot of the first 3 components. All the controls cluster in a relatively tight group to the right side, except for a few controls that clustered with the blast animals. The classifier is 83% accurate telling Blast from Control. Table 6 shows the top 8 weighted metabolites for each of the 10 leading components.

Dimensionality Reduction

Figure 5:
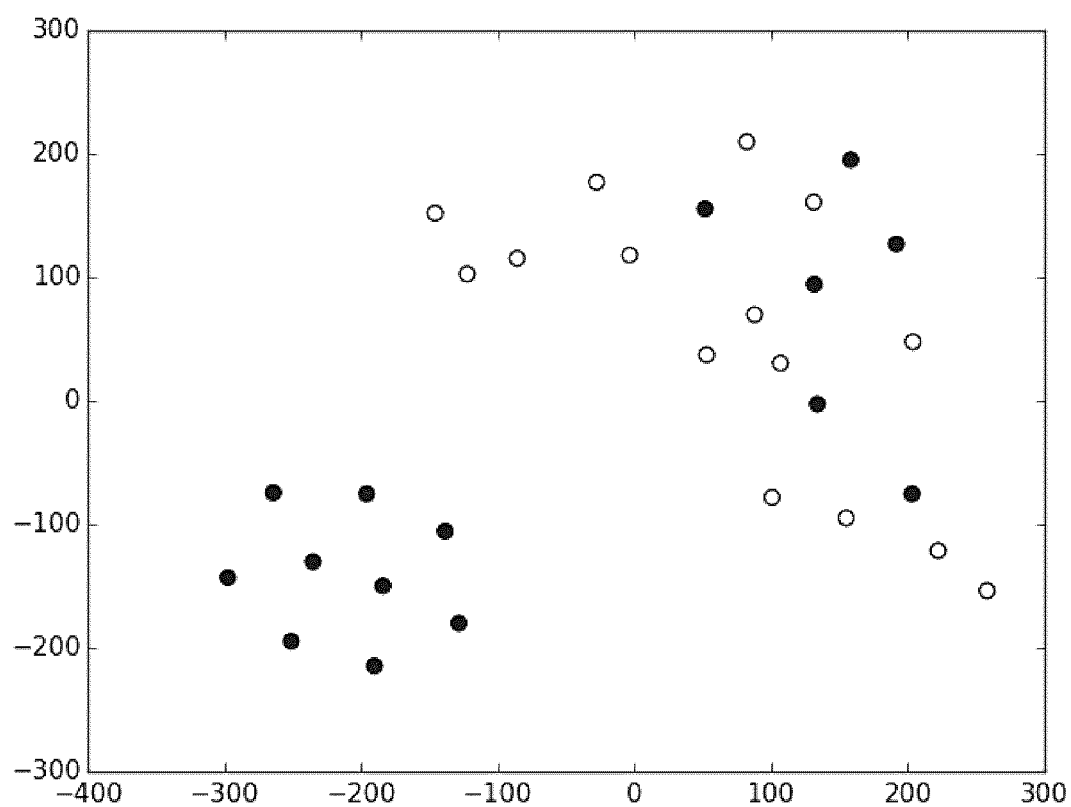
FIG. 5: Graph of individual subjects plotted in the reduced 2-dimensional space to illustrate the power of the t-SNE dimensionality reduction step (blast rats—open circles, control rats—filled circles).

The full metabolic dataset was reduced down to two dimensions using t-SNE, as the inherent dimensionality of the data was significantly lower that the number of metabolites (see FIG. 5). Following this dimensionality reduction step, a SVM was trained, with a linear kernel, to classify the rats as blast or control. Cross validation of our classifier using a leave-one-out approach demonstrated up to 86% (range 80-86%) accuracy rate in identifying a primary blast from a control rat (11-fold cross validated).

Figure 6:
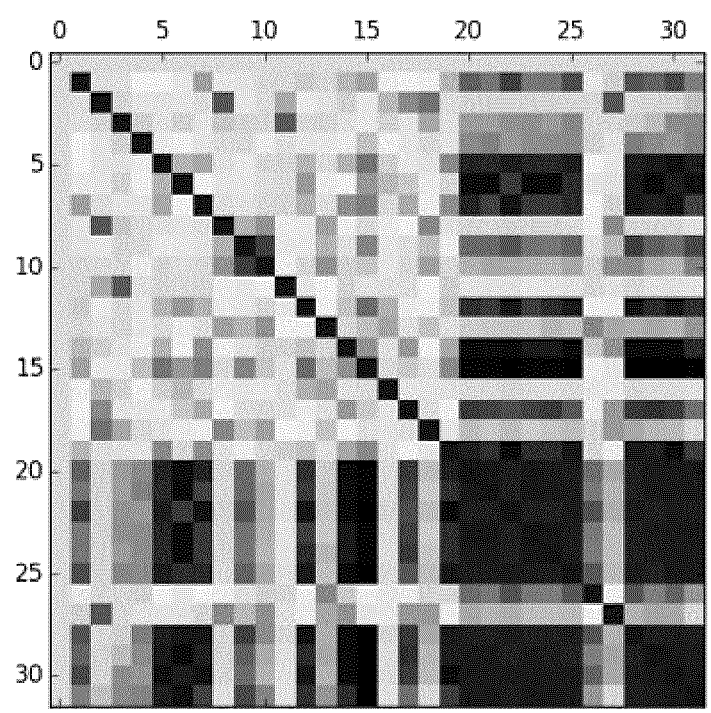
FIG. 6: Pearson product-moment coefficient to pairwise compare metabolite profiles between subjects.

FIG. 6 is a Pearson product-moment coefficient to pairwise compare metabolite profiles between subjects.

Figure 7:
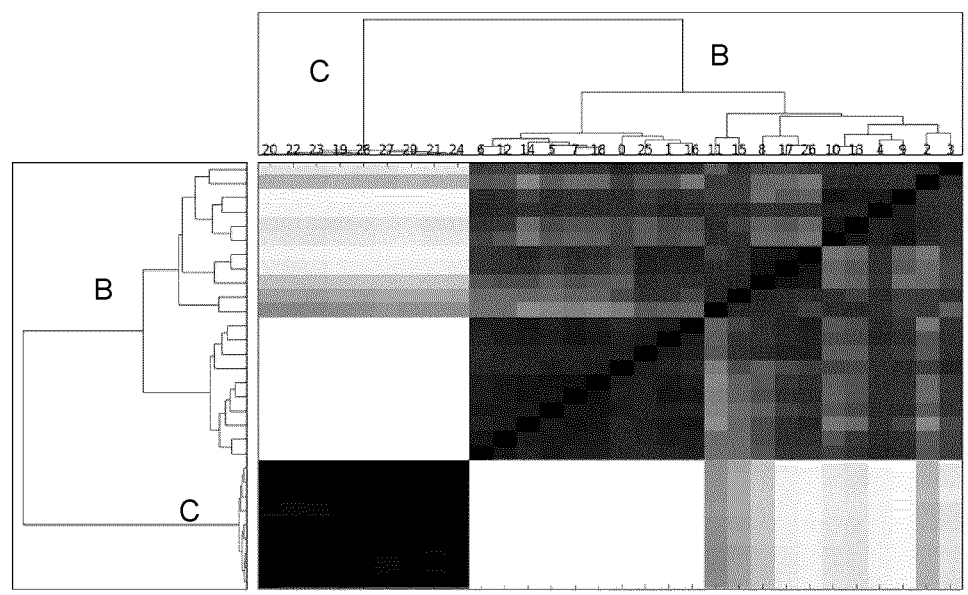
FIG. 7: Graph illustrating agglomerative complete-linkage hierarchical clustering, yielding 2 top level clusters: blast ("B") cluster (n=15), and control (C) cluster (n=15).
Figure 8:
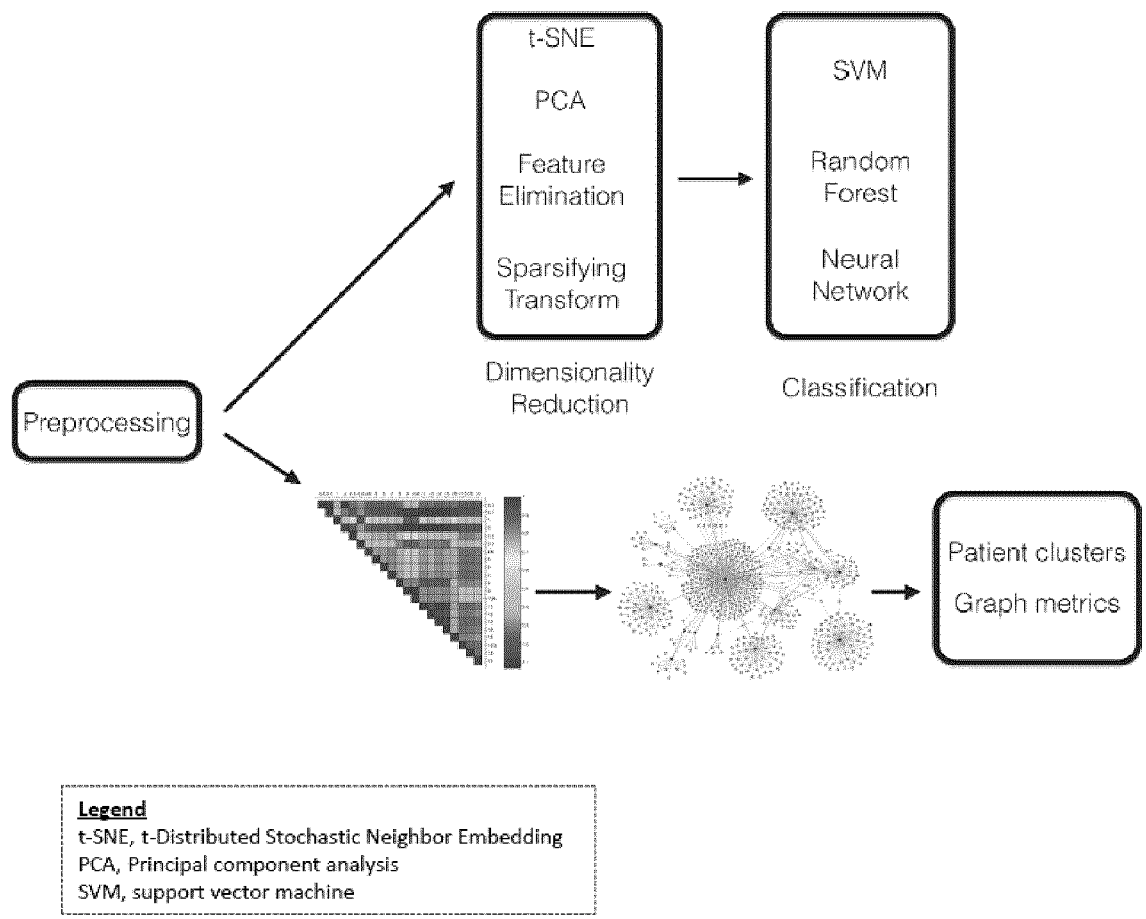
FIG. 8: Graph illustrating the approach to data analytics and modelling used in the embodiments of the present invention.

FIG. 7 illustrates a hierarchical clustering on the distance matrix of FIG. 6. The hierarchical clustering of FIG. 6 shows a big cluster on the left which are all controls (C). Bigger cluster on the right is mostly blast (B), but also a few controls. In FIGS. 6 and 7 labels 0-15 are blast rats, 16-31 are control rats.

Taking classification accuracy as our test statistic, we investigate the significance of our observed accuracy via permutation testing. We generated a null distribution by randomly shuffling class labels; training, and testing, a new classifier for each shuffled label set; and recording the classification rate. Generating 1000 null distributions with a permutation approach yields a $p<0.0001$ for the 80% (conservative) classification rate.

TABLE 6

PCA

| Comp.[1] 0 (Explained variance: 80.31%) | Comp. 1 (Explained variance: 4.5%) | Comp. 2 (Explained variance: 4.05%) | Comp. 3 (Explained variance: 2.13%) |
|---|---|---|---|
| PC ae C36:4 (0.103) | Asparagine (0.185) | C16 (0.253) | C18:2 (0.091) |
| PC ae C38:2 (0.103) | Aspartic acid (0.199) | C18 (0.244) | C2 (0.14) |
| PC ae C38:4 (0.103) | Ornithine (0.177) | C18:1 (0.252) | C4 (0.111) |
| PC ae C40:2 (0.103) | Carnosine (0.248) | C18:2 (0.229) | C5 (0.122) |
| PC ae C40:5 (0.103) | Histamine (0.33) | PC aa C30:2 (0.191) | C5:1 (0.13) |
| SM (OH) C14:1 (0.103) | Methionine sulfoxide (0.189) | SM C18:0 (0.183) | Dimethylarginine (0.144) |
| SM (OH) C22:1 (0.103) | Serotonin (0.183) | SM C18:1 (0.14) | cis-OH-Proline (0.384) |
| SM (OH) C22:2 (0.103) | Taurine (0.177) | SM C22:3 (0.207) | Serotonin (0.107) |

| Comp. 4 (Explained variance: 1.52%) | Comp. 5 (Explained variance: 1.31%) | Comp. 6 (Explained variance: 0.87%) | Comp. 7 (Explained variance: 0.81%) |
|---|---|---|---|
| C4 (0.108) | lysoPC a C28:0 (0.087) | C0 (0.128) | lysoPC a C28:1 (0.171) |
| PC aa C32:1 (0.072) | PC aa C30:2 (0.676) | C4 (0.119) | PC aa C30:2 (0.202) |
| PC ae C30:1 (0.096) | PC aa C38:1 (0.085) | PC ae C30:1 (0.197) | PC aa C32:1 (0.112) |
| SM C16:0 (0.074) | PC aa C42:0 (0.095) | PC ae C38:1 (0.151) | PC aa C32:2 (0.136) |
| SM C22:3 (0.354) | PC ae C30:1 (0.124) | Carnosine (0.158) | PC aa C34:4 (0.124) |
| Alanine (0.088) | Creatinine (0.117) | Histamine (0.19) | Carnosine (0.119) |
| Histamine (0.084) | cis-OH-Proline (0.309) | cis-OH-Proline (0.547) | Serotonin (0.49) |
| cis-OH-Proline (0.279) | Spermidine (0.158) | Serotonin (0.466) | Taurine (0.112) |

| Comp. 8 (Explained variance: 0.65%) | Comp. 9 (Explained variance: 0.54%) |
|---|---|
| PC aa C30:0 (0.156) | C5 (0.174) |
| PC aa C32:0 (0.245) | lysoPC a C20:4 (0.155) |
| PC aa C32:1 (0.114) | lysoPC a C28:1 (0.114) |
| PC aa C38:1 (0.134) | PC aa C30:0 (0.172) |
| PC ae C34:0 (0.214) | PC aa C32:0 (0.281) |
| PC ae C34:1 (0.126) | PC ae C34:0 (0.19) |
| PC ae C36:4 (0.131) | Histamine (0.202) |
| cis-OH-Proline (0.27) | Spermidine (0.116) |

[1]"Com." = Component

Example 3—Prognosis

Metabolomics

Plasma was assayed from three groups of participants: (1) participants having a first concussion episode, (2) participants with two or more reported concussions, and (3) control participants with no history of concussion. All concussed and non-concussed controls were clinically evaluated to determine concussion symptoms and severity. The participants were also assessed according to accepted standard diagnostic criteria. Plasma was assayed for metabolites by DI/LC-MS/MS and NMR.

PCA

Using PCA, the leading 10 components were demonstrated to account for the majority of the variance in the data, with each of the 10 components weighted across many of the underlying metabolites.

t-SNE

The full metabolic dataset was reduced down to two dimensions using t-SNE, as the inherent dimensionality of the data was significantly lower than the number of metabolites. Following this dimensionality reduction step, a support vector machine (SVM) was trained, with a linear kernel, to classify subjects as concussed or non-concussed. Cross validation of the classifier using a leave-one-out approach demonstrated a high percentage of accuracy rate in diagnosing a first concussion vs. multiple concussions.

Taking classification accuracy as our test statistic, the significance of the accuracy may be tested via permutation testing. A null distribution may be generated by randomly shuffling class labels; training and testing a new classifier for each shuffled label set and recording the classification rate.

The number of metabolites required to achieve reasonable classification accuracy may be minimized using a chi-square test to select informative metabolites in a univariate manner, and observe the percentage in classification accuracy with a minimized set of metabolites.

As a final step, the three different groups may be clustered by direct comparison of their metabolomics, including lipidome, profiles. Pearson product-moment coefficient may be computed for each pair of (normalized) subject metabolic profiles to yield a correlation matrix. Clusters may be optimally identified in this correlation matrix with agglomerative complete-linkage hierarchical clustering.

A receiver operating curve may be generated over a 4-fold cross-validation with a SVM, to demonstrate the performance of a binary classifier as its discrimination threshold is varied.

Example 4—Differentiating Types of ACNSI

Metabolomics

Plasma was assayed from six groups of participants: (1) mTBI participants having a concussion (concussion group), (2) mTBI participants having primary blast in blast-induced traumatic brain injury (blast group), (3) non-TBI participants with psychological distress (e.g. PTSD) brain injury (psychological group), (4) mTSI participants having spinal cord contusion (contusion group), (5) non-TSI participants (non-TSI group) and (6) control participants with no history of brain/spinal injury. The participants were assessed according to accepted standard diagnostic criteria.

Plasma was assayed for metabolites by DI/LC-MS/MS and NMR.

PCA

Using PCA, the leading 10 components were demonstrated to account for the majority of the variance in the data, with each of the 10 components weighted across many of the underlying metabolites.

t-SNE

The full metabolic dataset was reduced down to two dimensions using t-SNE, as the inherent dimensionality of the data was significantly lower than the number of metabolites. Following this dimensionality reduction step, a support vector machine (SVM) was trained, with a linear kernel, to classify subjects as concussed or non-concussed. Cross validation of the classifier using a leave-one-out approach demonstrated a high percentage of accuracy rate in diagnosing spinal injury, concussion, blast and psychological brain injuries.

Taking classification accuracy as our test statistic, the significance of the accuracy may be tested via permutation testing. A null distribution may be generated by randomly shuffling class labels; training and testing a new classifier for each shuffled label set and recording the classification rate.

The number of metabolites required to achieve reasonable classification accuracy may be minimized using a chi-square test to select informative metabolites in a univariate manner, and observe the percentage in classification accuracy with a minimized set of metabolites.

As a final step, the four different groups may be clustered by direct comparison of their metabolomics, including lipidome, profiles. Pearson product-moment coefficient may be computed for each pair of (normalized) subject metabolic profiles to yield a correlation matrix. Clusters may be optimally identified in this correlation matrix with agglomerative complete-linkage hierarchical clustering.

A receiver operating curve may be generated over a 4-fold cross-validation with a SVM, to demonstrate the performance of a binary classifier as its discrimination threshold is varied.

Through the embodiments that are illustrated and described, the currently contemplated best mode of making and using the invention is described. Without further elaboration, it is believed that one of ordinary skill in the art can, based on the description presented herein, utilize the present invention to the full extent. All publications cited herein are incorporated by reference.

Although the description above contains many specificities, these should not be construed as limiting the scope of the invention, but as merely providing illustrations of some of the presently embodiments of this invention.

What is claimed is:

1. A method of diagnosing mild traumatic brain injury (mTBI) in a subject comprising:
    (a) obtaining a metabolite profile from the subject;
    (b) using machine learning to compare the subject's profile with a predetermined set of metabolite profiles of mTBI and a predetermined set of metabolite profiles of non-mTBI (referred to as "control" or "normal") to determine if the subject has mTBI, the predetermined set of metabolite profiles of mTBI and non-mTBI comprise metabolites selected from:
    C0, C14:1, C14:2, C16, C18, C18:1, C18:2, C2, C3, C4, C5, C5-OH (C3-DC-M), C9, lysoPC a C16:0, lysoPC a C16:1, lysoPC a C17:0, lysoPC a C18:0, lysoPC a C18:1, lysoPC a C18:2, lysoPC a C20:3, lysoPC a C20:4, lysoPC a C26:0, lysoPC a C26:1, lysoPC a C28:0, lysoPC a C28:1, PC aa C24:0, PC aa C28:1, PC aa C30:0, PC aa C30:2, PC aa C32:0, PC aa C32:1, PC aa C32:2, PC aa C32:3, PC aa C34:1, PC aa C34:2, PC aa C34:3, PC aa C34:4, PC aa C36:0, PC aa C36:1, PC aa C36:2, PC aa C36:3, PC aa C36:4, PC aa C36:5, PC aa C36:6, PC aa C38:0, PC aa C38:1, PC aa C38:3, PC aa C38:4, PC aa C38:5, PC aa C38:6, PC aa C40:2, PC aa C40:3, PC aa C40:4, PC aa C40:5, PC aa C40:6, PC aa C42:0, PC aa C42:1, PC aa C42:4, PC aa C42:5, PC aa C42:6, PC ae C30:0, PC ae C30:1, PC ae C32:1, PC ae C32:2, PC ae C34:0, PC ae C34:1, PC ae C34:2, PC ae C34:3, PC ae C36:0, PC ae C36:1, PC ae C36:2, PC ae C36:3, PC ae C36:4, PC ae C36:5, PC ae C38:0, PC ae C38:1, PC ae C38:2, PC ae C38:3, PC ae C38:4, PC ae C38:5, PC ae C38:6, PC ae C40:1, PC ae C40:2, PC ae C40:3, PC ae C40:4, PC ae C40:5, PC ae C40:6, PC ae C42:1, PC ae C42:2, PC ae C42:3, PC ae C42:4, PC ae C42:5, PC ae C44:3, PC ae C44:4, PC ae C44:5, PC ae C44:6, SM (OH) C14:1, SM (OH) C16:1, SM (OH) C22:1, SM (OH) C22:2, SM (OH) C24:1, SM C16:0, SM C16:1, SM C18:0, SM C18:1, SM C20:2, SM C22:3, SM C24:0, SM C24:1, SM C26:0, SM C26:1, H1, Alanine, Arginine, Asparagine, Citrulline, Glutamine, Glutamic acid, Glycine, Histidine, Isoleucine, Leucine, Lysine, Methionine, Ornithine, Phenylalanine, Proline, Serine, Threonine, Tryptophan, Tyrosine, Valine, Acetyl-Ornithine, Asymmetricdimethylarginine, Total Dimethylarginine, alpha-Aminoadipic acid, Creatinine, Kynurenine, Methionine-Sulfoxide, trans-OH-Proline, Putrescine, Spermine, Taurine, 2-Hydroxybutyrate, 3-Hydroxybutyrate, 3-Hydroxyisovalerate, Acetate, Acetone, Betaine, Carnitine, Citrate, Creatine, Formate, Glucose, Glutamine, Glycerol, Lactate, Methanol, Propylene glycol, Pyruvate, and Succinate, and wherein the predetermined set of metabolite profiles of mTBI and non-mTBI include at least one phosphatidylcholine having one acyl- and one alkyl-bound fatty acids (PC ae); and
    (c) determining whether the subject is positive or negative for mTBI based on said comparison.

2. The method according to claim 1, wherein the predetermined profile of mTBI and non-mTBI are matched for one or more of: age, sex, activity, nutrition, body habitus, drugs and co-morbidity.

3. The method according to claim 1, wherein the subject's metabolite profile and the predetermined set of metabolite profiles are obtained using metabolomics.

4. The method of claim 3, wherein the metabolomics is performed with one or more of high performance liquid chromatography, thin layer chromatography, electrochemical analysis, mass spectroscopy (MS), refractive index spectroscopy, ultra-violet spectroscopy, fluorescent analysis, radiochemical analysis, near-infrared spectroscopy, nuclear magnetic resonance (NMR), light scattering analysis, gas chromatography (GC), or GC coupled with MS, direct injection (DI) coupled with LC-MS/MS.

5. The method of claim 1, wherein metabolite profiles are obtained from a biological test sample selected from the group consisting of: whole blood, blood plasma, blood serum, saliva, synovial fluid, urine, spinal fluid, bronchoalveolar lavage, tears, sweat, and extracts.

6. The method of claim 1, wherein the metabolite profile is a lipidome.

7. The method according to claim 1, wherein the mTBI is concussion and the predetermined set of metabolite profiles of mTBI and non-mTBI include the following metabolites: C5, PC aa C32:1, PC aa C32:2, PC aa C36:5, PC aa C36:6, PC ae C34:0, PC ae C34:3, PC ae C36:0, PC ae C36:1, PC ae C36:2, PC ae C38:1, PC ae C38:2, PC ae C38:3, Putrescine, Formate, Methanol, and Succinate.

8. The method according to claim 1, wherein the mTBI is concussion and the predetermine set of metabolite profiles of mTBI and non-mTBI include the following metabolites: C5, PC aa C30:2, PC aa C32:0, PC aa C32:1, PC aa C32:2, PC aa C32:3, PC aa C34:4, PC aa C36:6, PC aa C42:6, PC ae C30:0, PC ae C30:1, PC ae C32:1, PC ae C34:0, PC ae C34:2, PC ae C34:3, PC ae C36:0, PC ae C36:2, PC ae C38:1, PC ae C38:3, SM C22:3, SM C24:0, SM C24:1, alpha-Aminoadipic acid, trans-OH-Proline, Putrescine, Betaine, Formate, Glucose, Glycerol, Methanol, and Serine.

9. The method according to claim 1, wherein the mTBI is selected from concussion and primary blast in blast-induced traumatic brain.

10. The method of claim 1, wherein when the subject is positive for mTBI based on said comparison and is being treated for mTBI, the method further comprises obtaining metabolite profiles from the subject at different times during the treatment of the subject;
using the machine learning to compare the subject's profiles at each of the different times during the treatment with the predetermined set of metabolite profiles of non-mTBI and the predetermined set of metabolite profiles of non-mTBI to follow the efficiency of the medical intervention in the subject; and
continue the treatment of the subject for mTBI as long as the subject is positive for mTBI at each of the different times during the treatment.

11. The method of claim 1, wherein the mTBI is primary blast traumatic brain Injury and the predetermine set of metabolite profiles of mTBI and non-mTBI include the following metabolites: PC ae C36:4, PC ae C38:2, PC ae C38:4, PC ae C40:2, PC ae C40:5, SM (OH) C14:1, SM (OH) C22:1, and SM (OH) C22:2.

12. The method of claim 1, wherein (I) the metabolite profile of the subject and the predetermined sets of mTBI and non-mTBI profiles are provided as sets of multi-dimensional metabolomics data, and step (b) comprises applying to the sets of multi-dimensional metabolomics data (i) a dimensionality reduction, (ii) a feature selection, or (iii) both dimensionality reduction and feature selection, to obtain a reduced metabolomics data set, or
(II) step (b) comprises normalizing the set metabolite profile of the subject and the sets of predetermined metabolite profiles of mTBI and non-mTBI to obtain matrix, and performing principal components analysis directly on the metabolite matrix.

13. The method of claim 1, wherein the method further comprises treating the subject for mTBI only when the subject is positive for mTBI.

14. A computer program product for use in conjunction with a computer system, the computer program product comprising a non-transitory computer readable storage medium and a computer program mechanism embedded therein, the computer program mechanism comprising executable instructions for performing a method of diagnosing mild traumatic brain injury (mTBI) in a subject, said executable instructions comprising:
(a) using machine learning to compare the subject's profile with a predetermined set of metabolite profiles of mTBI and a predetermined set of metabolite profiles of non-mTBI to determine if the subject has mTBI, the predetermined set of metabolite profiles of mTBI and non-mTBI comprise metabolites selected from C0, C14:1, C14:2, C16, C18, C18:1, C18:2, C2, C3, C4, C5, C5-OH (C3-DC-M), C9, lysoPC a C16:0, lysoPC a C16:1, lysoPC a C17:0, lysoPC a C18:0, lysoPC a C18:1, lysoPC a C18:2, lysoPC a C20:3, lysoPC a C20:4, lysoPC a C26:0, lysoPC a C26:1, lysoPC a C28:0, lysoPC a C28:1, PC aa C24:0, PC aa C28:1, PC aa C30:0, PC aa C30:2, PC aa C32:0, PC aa C32:1, PC aa C32:2, PC aa C32:3, PC aa C34:1, PC aa C34:2, PC aa C34:3, PC aa C34:4, PC aa C36:0, PC aa C36:1, PC aa C36:2, PC aa C36:3, PC aa C36:4, PC aa C36:5, PC aa C36:6, PC aa C38:0, PC aa C38:1, PC aa C38:3, PC aa C38:4, PC aa C38:5, PC aa C38:6, PC aa C40:2, PC aa C40:3, PC aa C40:4, PC aa C40:5, PC aa C40:6, PC aa C42:0, PC aa C42:1, PC aa C42:4, PC aa C42:5, PC aa C42:6, PC ae C30:0, PC ae C30:1, PC ae C32:1, PC ae C32:2, PC ae C34:0, PC ae C34:1, PC ae C34:2, PC ae C34:3, PC ae C36:0, PC ae C36:1, PC ae C36:2, PC ae C36:3, PC ae C36:4, PC ae C36:5, PC ae C38:0, PC ae C38:1, PC ae C38:2, PC ae C38:3, PC ae C38:4, PC ae C38:5, PC ae C38:6, PC ae C40:1, PC ae C40:2, PC ae C40:3, PC ae C40:4, PC ae C40:5, PC ae C40:6, PC ae C42:1, PC ae C42:2, PC ae C42:3, PC ae C42:4, PC ae C42:5, PC ae C44:3, PC ae C44:4, PC ae C44:5, PC ae C44:6, SM (OH) C14:1, SM (OH) C16:1, SM (OH) C22:1, SM (OH) C22:2, SM (OH) C24:1, SM C16:0, SM C16:1, SM C18:0, SM C18:1, SM C20:2, SM C22:3, SM C24:0, SM C24:1, SM C26:0, SM C26:1, H1, Alanine, Arginine, Asparagine, Citrulline, Glutamine, Glutamic acid, Glycine, Histidine, Isoleucine, Leucine, Lysine, Methionine, Ornithine, Phenylalanine, Proline, Serine, Threonine, Tryptophan, Tyrosine, Valine, Acetyl-Ornithine, Asymmetricdimethylarginine, Total Dimethylarginine, alpha-Aminoadipic acid, Creatinine, Kynurenine, Methionine-Sulfoxide, trans-OH-Proline, Putrescine, Spermine, Taurine, 2-Hydroxybutyrate, 3-Hydroxybutyrate, 3-Hydroxyisovalerate, Acetate, Acetone, Betaine, Carnitine, Citrate, Creatine, Formate, Glucose, Glutamine, Glycerol, Lactate, Methanol, Propylene glycol, Pyruvate, and Succinate, and wherein the predetermined set of metabolite profiles of mTBI and non-mTBI include at least one phosphatidylcholine having one acyl- and one alkyl-bound fatty acids (PC ae); and
(b) determining if the subject has mTBI based on said comparison.

15. The computer program product of claim 14, wherein the program mechanism further comprises executable instructions for: (i) identifying metabolites in a first set of biological samples from a population of subjects known to have mTBI and in a second set of biological samples from a population of control non-mTBI (referred to as "normal") subjects thereby obtaining the predetermined set of mTBI profiles and the predetermined set of non-mTBI set of profiles.

16. The computer program product of claim 14, wherein an initial dimensionality reduction is performed on the subject's metabolite profile and in the predetermined set of mTBI profiles and the predetermined set of non-mTBI profiles by t-SNE.

17. The computer program product of claim 14, wherein the mTBI is concussion and the metabolite profiles include the following metabolites: C5, PC aa C32:1, PC aa C32:2, PC aa C36:5, PC aa C36:6, PC ae C34:0, PC ae C34:3, PC ae C36:0, PC ae C36:1, PC ae C36:2, PC ae C38:1, PC ae C38:2, PC ae C38:3, Putrescine, Formate, Methanol, and Succinate.

18. The computer program product of claim 14, wherein the mTBI is concussion and the predetermine set of metabolite profiles of mTBI and non-mTBI include the following metabolites: C5, PC aa C30:2, PC aa C32:0, PC aa C32:1, PC aa C32:2, PC aa C32:3, PC aa C34:4, PC aa C36:6, PC aa C42:6, PC ae C30:0, PC ae C30:1, PC ae C32:1, PC ae C34:0, PC ae C34:2, PC ae C34:3, PC ae C36:0, PC ae C36:2, PC ae C38:1, PC ae C38:3, SM C22:3, SM C24:0, SM C24:1, alpha-Aminoadipic acid, trans-OH-Proline, Putrescine, Betaine, Formate, Glucose, Glycerol, Methanol, and Serine.

19. The computer program product of claim 14, wherein the mTBI is primary blast traumatic brain Injury and the predetermine set of metabolite profiles of mTBI and non-mTBI include the following metabolites: PC ae C36:4, PC ae C38:2, PC ae C38:4, PC ae C40:2, PC ae C40:5, SM (OH) C14:1, SM (OH) C22:1, and SM (OH) C22:2.

20. The computer program product of claim 14, wherein (I) the metabolite profile of the subject and the predetermined sets of mTBI and non-mTBI profiles are provided as sets of multi-dimensional metabolomics data, and step (b) comprises applying to the sets of multi-dimensional metabolomics data (i) a dimensionality reduction, (ii) a feature selection, or (iii) both dimensionality reduction and feature selection, to obtain a reduced metabolomics data set, or (II) step (b) comprises normalizing the set metabolite profile of the subject and the sets of predetermined metabolite profiles of mTBI and non-mTBI to obtain matrix, and performing principal components analysis directly on the metabolite matrix.

21. A method of diagnosing mild traumatic brain injury (mTBI) in a subject comprising:
(a) obtaining a metabolite profile from the subject;
(b) using machine learning to compare the subject's profile with a predetermined set of metabolite profiles of mTBI and a predetermined set of metabolite profiles of non-mTBI (referred to as "control" or "normal") to determine if the subject has mTBI, the predetermined set of metabolite profiles of mTBI and non-mTBI comprise metabolites selected from:
C0, C14:1, C14:2, C16, C18, C18:1, C18:2, C2, C3, C4, C5, 05-OH (C3-DC-M), C9, lysoPC a C16:0, lysoPC a C16:1, lysoPC a C17:0, lysoPC a C18:0, lysoPC a C18:1, lysoPC a C18:2, lysoPC a C20:3, lysoPC a C20:4, lysoPC a C26:0, lysoPC a C26:1, lysoPC a C28:0, lysoPC a C28:1, PC aa C24:0, PC aa C28:1, PC aa C30:0, PC aa C30:2, PC aa C32:0, PC aa C32:1, PC aa C32:2, PC aa C32:3, PC aa C34:1, PC aa C34:2, PC aa C34:3, PC aa C34:4, PC aa C36:0, PC aa C36:1, PC aa C36:2, PC aa C36:3, PC aa C36:4, PC aa C36:5, PC aa C36:6, PC aa C38:0, PC aa C38:1, PC aa C38:3, PC aa C38:4, PC aa C38:5, PC aa C38:6, PC aa C40:2, PC aa C40:3, PC aa C40:4, PC aa C40:5, PC aa C40:6, PC aa C42:0, PC aa C42:1, PC aa C42:4, PC aa C42:5, PC aa C42:6, PC ae C30:0, PC ae C30:1, PC ae C32:1, PC ae C32:2, PC ae C34:0, PC ae C34:1, PC ae C34:2, PC ae C34:3, PC ae C36:0, PC ae C36:1, PC ae C36:2, PC ae C36:3, PC ae C36:4, PC ae C36:5, PC ae C38:0, PC ae C38:1, PC ae C38:2, PC ae C38:3, PC ae C38:4, PC ae C38:5, PC ae C38:6, PC ae C40:1, PC ae C40:2, PC ae C40:3, PC ae C40:4, PC ae C40:5, PC ae C40:6, PC ae C42:1, PC ae C42:2, PC ae C42:3, PC ae C42:4, PC ae C42:5, PC ae C44:3, PC ae C44:4, PC ae C44:5, PC ae C44:6, SM (OH) C14:1, SM (OH) C16:1, SM (OH) C22:1, SM (OH) C22:2, SM (OH) C24:1, SM C16:0, SM C16:1, SM C18:0, SM C18:1, SM C20:2, SM C22:3, SM C24:0, SM C24:1, SM C26:0, SM C26:1, H1, Alanine, Arginine, Asparagine, Citrulline, Glutamine, Glutamic acid, Glycine, Histidine, Isoleucine, Leucine, Lysine, Methionine, Ornithine, Phenylalanine, Proline, Serine, Threonine, Tryptophan, Tyrosine, Valine, Acetyl-Ornithine, Asymmetricdimethylarginine, Total Dimethylarginine, alpha-Aminoadipic acid, Creatinine, Kynurenine, Methionine-Sulfoxide, trans-OH-Proline, Putrescine, Spermine, Taurine, 2-Hydroxybutyrate, 3-Hydroxybutyrate, 3-Hydroxyisovalerate, Acetate, Acetone, Betaine, Carnitine, Citrate, Creatine, Formate, Glucose, Glutamine, Glycerol, Lactate, Methanol, Propylene glycol, Pyruvate, and Succinate; and
(c) determining whether the subject is positive or negative for mTBI based on said comparison,
wherein (I) the metabolite profile of the subject and the predetermined sets of mTBI and non-mTBI profiles are provided as sets of multi-dimensional metabolomics data, and step (b) comprises applying to the sets of multi-dimensional metabolomics data (i) a dimensionality reduction, (ii) a feature selection, or (iii) both dimensionality reduction and feature selection, to obtain a reduced metabolomics data set, or
(II) step (b) comprises normalizing the set metabolite profile of the subject and the sets of predetermined metabolite profiles of mTBI and non-mTBI to obtain matrix, and performing principal components analysis directly on the metabolite matrix.

\* \* \* \* \*